United States Patent
Foltz et al.

(10) Patent No.: US 9,114,186 B2
(45) Date of Patent: Aug. 25, 2015

(54) STERILIZATION PROCESS CHALLENGE DEVICE

(75) Inventors: William E. Foltz, Cottage Grove, MN (US); Steven S. Kirckof, Woodbury, MN (US); Lawrence D. Fosler, Cottage Grove, MN (US); Joshua M. Schmitz, Flemington, NJ (US); Barry W. Robole, Woodville, WI (US); Chad M. Herrlein, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1293 days.

(21) Appl. No.: 12/991,023

(22) PCT Filed: May 5, 2009

(86) PCT No.: PCT/US2009/042790
§ 371 (c)(1),
(2), (4) Date: Nov. 4, 2010

(87) PCT Pub. No.: WO2009/137442
PCT Pub. Date: Nov. 12, 2009

(65) Prior Publication Data
US 2011/0064606 A1    Mar. 17, 2011

Related U.S. Application Data

(60) Provisional application No. 61/050,513, filed on May 5, 2008, provisional application No. 61/112,149, filed on Nov. 6, 2008.

(51) Int. Cl.
*C12Q 1/22* (2006.01)
*A61L 2/28* (2006.01)

(52) U.S. Cl.
CPC .... *A61L 2/28* (2013.01); *C12Q 1/22* (2013.01)

(58) Field of Classification Search
CPC ............... A61L 2/00; A61L 2/16; A61L 2/26; A61L 2/28; C12M 1/34; C12M 1/3446; C12M 1/3476; C12Q 1/00; C12Q 1/02; C12Q 1/22
USPC .............................................. 422/3, 312, 430
See application file for complete search history.

(56) References Cited

U.S. PATENT DOCUMENTS

| | | | |
|---|---|---|---|
| 3,981,683 | A | 9/1976 | Larsson et al. |
| 4,115,068 | A | 9/1978 | Joslyn et al. |

(Continued)

FOREIGN PATENT DOCUMENTS

| | | |
|---|---|---|
| AU | 2004224765 B2 | 10/2004 |
| EP | 0432871 | 7/1990 |

(Continued)

OTHER PUBLICATIONS

The European Standard EN 867-5:2001 entitled Non-Biological Systems for use in Sterilizers, dated Sep. 25, 2005, 12 pages.

(Continued)

*Primary Examiner* — Jill Warden

(57) ABSTRACT

A sterilization process challenge device comprising a solid body comprised of walls which define a space, wherein the space can fully contain a sterilization indicator and a volume of gas of at least 5 cubic centimeters and not more than 1000 cubic centimeters; a flow restrictor associated with the solid body such that any flow of the gas out of the space and any flow of a sterilant into the space is restricted; wherein the sterilization indicator indicates whether or not it has been contacted by the sterilant for a time and at a temperature sufficient to sterilize an article; and wherein the walls of the solid body are impervious to the sterilant and have a thickness of at least 0.3 centimeter, methods of using the device and a kit including the device are disclosed.

9 Claims, 7 Drawing Sheets

(56) References Cited

U.S. PATENT DOCUMENTS

| | | | |
|---|---|---|---|
| 4,612,872 | A | 9/1986 | Whelchel et al. |
| 4,636,472 | A | 1/1987 | Bruso |
| 4,717,661 | A | 1/1988 | McCormick et al. |
| 4,748,003 | A * | 5/1988 | Riley .................. 422/112 |
| 4,863,867 | A | 9/1989 | Joyce et al. |
| 4,914,034 | A | 4/1990 | Welsh et al. |
| 5,066,464 | A | 11/1991 | Augurt |
| 5,435,971 | A | 7/1995 | Dyckman |
| 5,565,634 | A | 10/1996 | Graessle et al. |
| 5,571,476 | A * | 11/1996 | Newman .................. 422/26 |
| 5,789,175 | A | 8/1998 | Priest |
| 5,872,004 | A | 2/1999 | Bolsen |
| 5,916,816 | A | 6/1999 | Read |
| 5,942,408 | A | 8/1999 | Christensen et al. |
| 5,989,852 | A | 11/1999 | Hendricks |
| 6,051,187 | A | 4/2000 | Hughes |
| 6,323,032 | B1 | 11/2001 | Kuepper et al. |
| 6,352,837 | B1 | 3/2002 | Witcher et al. |
| 6,623,955 | B2 | 9/2003 | Matner et al. |
| 6,630,352 | B1 | 10/2003 | Reiner et al. |
| 6,653,096 | B1 | 11/2003 | Christensen et al. |
| 7,045,343 | B2 | 5/2006 | Witcher et al. |
| 7,091,042 | B2 | 8/2006 | Lemus et al. |
| 7,247,482 | B2 | 7/2007 | Lemus et al. |
| 2001/0006610 | A1 | 7/2001 | Miller et al. |
| 2002/0022246 | A1 | 2/2002 | Lin et al. |
| 2003/0157588 | A1 | 8/2003 | Matner et al. |
| 2003/0162243 | A1* | 8/2003 | Foltz et al. .................. 435/31 |
| 2004/0256269 | A1* | 12/2004 | Gleichauf et al. ............ 206/439 |
| 2005/0268573 | A1 | 12/2005 | Yan |
| 2006/0234330 | A1 | 10/2006 | Lemus et al. |
| 2011/0064606 | A1 | 3/2011 | Foltz et al. |

FOREIGN PATENT DOCUMENTS

| | | |
|---|---|---|
| EP | 0419282 A1 | 9/1990 |
| EP | 628814 A1 | 12/1994 |
| EP | 12012 | 5/2002 |
| EP | 1308174 | 5/2003 |
| EP | 1468701 B1 | 6/2005 |
| EP | 1550467 A1 | 7/2005 |
| GB | 1316808 A | 5/1973 |
| GB | 2186974 | 1/1987 |
| GB | 2180933 | 4/1987 |
| JP | 03-121072 | 5/1991 |
| JP | 03-159650 | 7/1991 |
| JP | 2006-296850 | 11/2006 |
| WO | WO 94-28164 A | 12/1994 |
| WO | WO 95-32742 A | 12/1995 |
| WO | WO 99-20790 A | 4/1999 |
| WO | WO 99-62569 A | 12/1999 |
| WO | 02/056923 | 7/2002 |
| WO | WO 03-012459 | 2/2003 |
| WO | WO 03033034 | 4/2003 |
| WO | WO 2004-084956 A1 | 10/2004 |
| WO | WO 2005-056061 A1 | 6/2005 |
| WO | WO 2008/079469 | 7/2008 |
| WO | WO 2008-082728 A | 7/2008 |
| WO | WO 2010/054033 | 5/2010 |
| WO | WO 2010-054095 | 5/2010 |

OTHER PUBLICATIONS

Japanese Society of Medical Instrumentation entitled Guideline for Sterility Assurance in Healthcare Setting, dated Sep. 1, 2005, 6 pages.

ANSI/AAMI/ISO 11140-1:2005, Sterilization of health care products—Chemical indicators.

ANSI/AAMI/ISO 11138-1:2006, Sterilization of health care products—health care products—Biological Indicators.

Kaiser, "Which *Chemical Indicators Should be Used in a Process Challenge Device System(PCD)*" 0942-6086 Zentralsterilisation—Central Service, 15()46—Central Service The British Library.

PCD, Features and Benifits "http://www.pcd1.com/features.html" Oct. 6, 2006.

PCD, Directions For Use, "http://www/pcd1.com/directions.html" Oct. 6, 2006.

PCD, Product Information "http://www.pcd1.com/Products.html" Oct. 6, 2006.

PCD, Ordering Information "http://www.pcd1.com/ordering.html" Oct. 6, 2006.

PCD, Validation Guide "http://www.pcd1.com/validation.html" Oct. 6, 2006.

PCD, Frequently Asked Questions "http://www.pcd1.com/faq.html" Oct. 6, 2006.

* cited by examiner

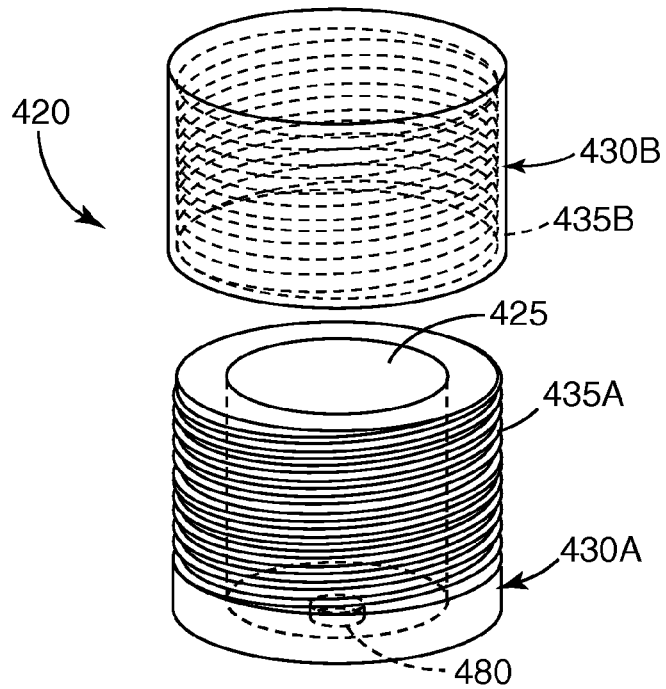
*Fig. 4*
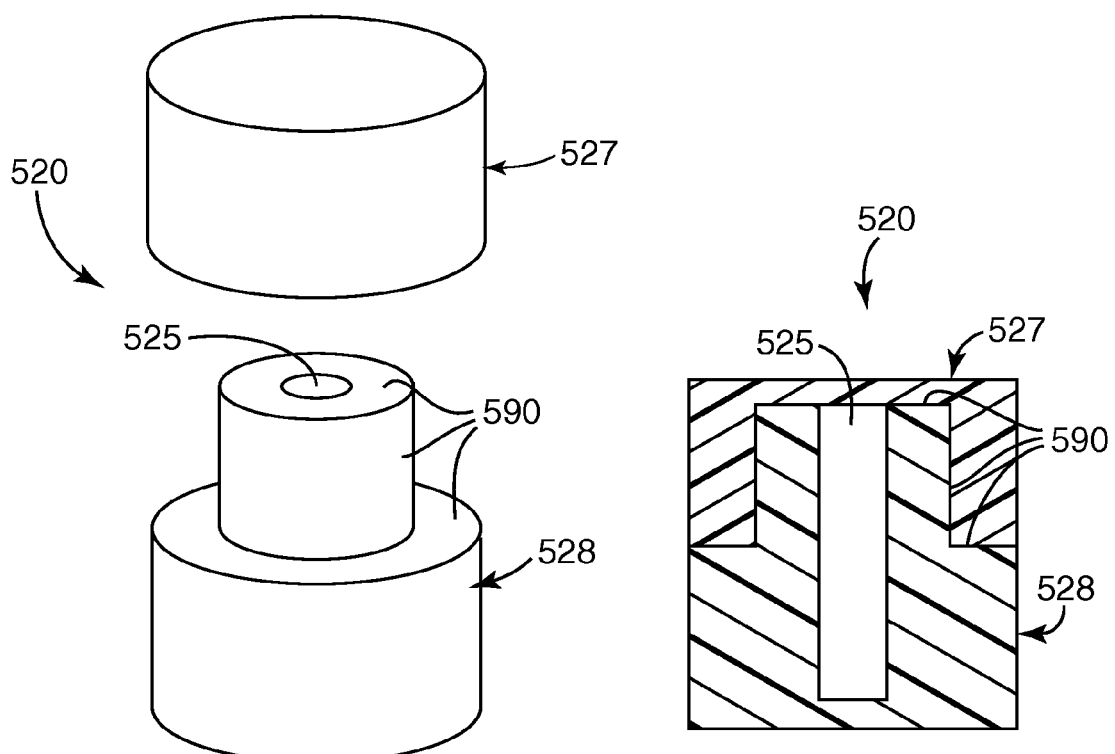
*Fig. 5*  *Fig. 5A*

STERILIZATION PROCESS CHALLENGE DEVICE

CROSS REFERENCE TO RELATED APPLICATIONS

This application is the National Stage filing under 35 U.S.C. 371 of International Application No. PCT/US2009/042790, filed May 5, 2009, which claims the benefit of U.S. Provisional Application No. 61/050,513, filed May 5, 2008, and U.S. Provisional Application No. 61/112,149, filed Nov. 6, 2008, both of which are incorporated herein by reference in their entirety.

BACKGROUND

A variety of products and articles, including medical instruments, must be sterilized prior to use to prevent biocontamination of a sample, an organism, a wound site, or the like. A number of sterilization processes are used which involve contacting the product or article with a fluid sterilant, such as a gaseous sterilant. Examples of such sterilants include, for example, steam, ethylene oxide, hydrogen peroxide, and the like.

The products and articles are generally packaged such that the sterilant can pass through the packaging, but microorganisms cannot pass through. Even though the sterilant can pass, the packaging restricts the movement of the sterilant to the product or article. Moreover, some products and articles include spaces within them that can only be reached by the sterilant via a restricted path. For example, endoscopes often include a long, narrow channel through which the sterilant must pass in order to sterilize the endoscope. These and other forms of restrictions associated with products and articles to be sterilized must be taken into account when employing a sterilization process, so that all surfaces of the product or article are exposed to the sterilant for a time sufficient to cause sterilization.

Monitoring for sufficient sterilization is generally carried out by placing an appropriate sterilization indicator along with the product and/or article to be sterilized within a sterilization chamber. A variety of sterilization indicators, including biological and chemical indicators, are known and used for this purpose. However, to take into account the above described restrictions encountered in the various products and articles, the sterilization indicator has been placed in a challenge device which restricts the flow of sterilant to the indicator using a long tortuous path. While such devices have been useful, they have not always been convenient to use and/or they have not always provided a close correlation between an indication of complete sterilization and actual complete sterilization of the product or article.

As such, there continues to be an interest in and a need for challenge devices which are convenient to use and provide a more reliable correlation between the indication of complete sterilization and actual complete sterilization of a product or article.

SUMMARY OF THE INVENTION

The present invention provides a sterilization process challenge device comprising:

a solid body comprised of walls which define a space, wherein the space can fully contain a sterilization indicator and a volume of gas of at least 5 cubic centimeters and not more than 1000 cubic centimeters;

a flow restrictor associated with the solid body such that any flow of the gas out of the space and any flow of a sterilant into the space is restricted;

wherein the sterilization indicator indicates whether or not it has been contacted by the sterilant for a time and at a temperature sufficient to sterilize an article;

wherein the walls of the solid body are impervious to the sterilant, and wherein the walls have a thickness of at least 0.3 centimeter.

The volume of gas contained within the space also containing the sterilization indicator has been found to provide a resistance to the sterilant which can be controlled and used effectively to provide a sterilization challenge device which can correlate well with sterilization of a variety of products and articles and quantities thereof. Moreover, the solid body, the walls of which do not absorb sterilant or allow sterilant to diffuse or permeate through, except where an opening is provided for the sterilant to enter the space defined by the walls, acts to control the time required for the sterilization indicator to reach a temperature desired for efficient sterilization. Further control of the resistance to the sterilant is provided by the flow restrictor. This is accomplished in one way by controlling the flow of gas, such as air, nitrogen, carbon dioxide, or other unreactive gas out of the space defined by the walls of the solid body. Displacement of this gas is necessary in order for the sterilant to fill the space and contact the indicator. In another way, resistance to the sterilant is provided by controlling the flow of sterilant into the space.

For certain embodiments, the above device further comprises a container, wherein the solid body is sealed within the container, the flow restrictor is attached to or is part of the container, and any gas flow out of and any sterilant flow into the container are restricted by the flow restrictor. For certain of these embodiments, a volume of gas of at least 5 cubic centimeters is contained within the container in addition to the volume of gas contained in the space defined by the walls of the solid body.

In another embodiment, there is provided a sterilization process challenge device comprising:

a solid body comprised of walls which define a space, wherein the space can fully contain a sterilization indicator;

a container, wherein the solid body is sealed within the container, and a volume of gas of at least 5 cubic centimeters is contained within the container;

a flow restrictor attached to or which is part of the container such that any flow of the gas out of the container and any flow of a sterilant into the container is restricted;

wherein the sterilization indicator indicates whether or not it has been contacted by the sterilant for a time and at a temperature sufficient to sterilize an article;

wherein the walls of the solid body are impervious to the sterilant, and wherein the walls have a thickness of at least 0.3 centimeter.

The volume of gas within the container provides a resistance to the sterilant as described above for the volume of gas contained within the space with the sterilization indicator. It has been found that including this volume of gas, which is to be displaced by the sterilant before effective contact of the indicator by the sterilant can occur, provides an effective challenge to achieving sterilization conditions.

In another embodiment, there is provided a method of controlling the level of resistance to a sterilization process provided by a sterilization process challenge device, the method comprising:
  providing a sterilization process challenge device comprising:
    a solid body comprised of walls which define a space, wherein the space can fully contain a sterilization indicator and a volume of gas of at least 5 cubic centimeters;
    a flow restrictor associated with the solid body such that any flow of the gas out of the space and any flow of a sterilant into the space is restricted;
    wherein the sterilization indicator indicates whether or not it has been contacted by the sterilant for a time and at a temperature sufficient to sterilize an article;
    wherein the walls of the solid body are impervious to the sterilant, and wherein the walls have a thickness of at least 0.3 centimeter; and
  adjusting the sterilization process challenge device to provide a targeted level of resistance to a sterilization process; wherein adjusting comprises a step selected from the group consisting of:
    adjusting the thickness of the walls,
    adjusting the thermal diffusivity of the solid body,
    adjusting the volume of the gas,
    adjusting the flow restrictor to increase or decrease the flow of the gas out of the space and the flow of the sterilant gas into the space defined by the walls of the solid body, and
    a combination thereof.

In another embodiment, there is provided a method of controlling the level of resistance to a sterilization process provided by a sterilization process challenge device, the method comprising:
  providing a sterilization process challenge device comprising:
    a solid body comprised of walls which define a space, wherein the space can fully contain a sterilization indicator;
    a container, wherein the solid body is sealed within the container, and a volume of gas of at least 5 cubic centimeters is contained within the container;
    a flow restrictor attached to or which is part of the container such that any flow of the gas out of the container and any flow of a sterilant into the container is restricted;
    wherein the sterilization indicator indicates whether or not it has been contacted by the sterilant for a time and at a temperature sufficient to sterilize an article;
    wherein the walls of the solid body are impervious to the sterilant, and wherein the walls have a thickness of at least 0.3 centimeter; and
  adjusting the sterilization process challenge device to provide a targeted level of resistance to a sterilization process; wherein adjusting comprises a step selected from the group consisting of:
    adjusting the thickness of the walls,
    adjusting the thermal diffusivity of the solid body,
    adjusting the volume of the gas,
    adjusting the flow restrictor to increase or decrease the flow of the gas out of the space and the flow of the sterilant gas into the space defined by the walls of the solid body, and
    a combination thereof.

In another embodiment, there is provided a method of determining the effectiveness of a sterilization process for sterilizing an article, the method comprising:
  providing a sterilization process challenge device comprising:
    a solid body comprised of walls which define a space, wherein the space fully contains a sterilization indicator and a volume of gas of at least 5 cubic centimeters;
    a flow restrictor associated with the solid body such that any flow of the gas out of the space and any flow of a sterilant into the space is restricted;
    wherein the sterilization indicator indicates whether or not it has been contacted by the sterilant for a time and at a temperature sufficient to sterilize an article;
    wherein the walls of the solid body are impervious to the sterilant, and wherein the walls have a thickness of at least 0.3 centimeter;
  placing the sterilization process challenge device in a sterilization chamber containing the article;
  exposing the sterilization process challenge device and the article to the sterilant and to an elevated temperature; and
  determining whether or not the sterilization indicator indicates that it has been contacted by the sterilant for a time and at a temperature sufficient to sterilize the article.

In another embodiment, there is provided a method of determining the effectiveness of a sterilization process for sterilizing an article, the method comprising:
  providing a sterilization process challenge device comprising:
    a solid body comprised of walls which define a space, wherein the space fully contains a sterilization indicator;
    a container, wherein the solid body is sealed within the container, and a volume of gas of at least 5 cubic centimeters is contained within the container;
    a flow restrictor attached to or which is part of the container such that any flow of the gas out of the container and any flow of a sterilant into the container is restricted;
    wherein the sterilization indicator indicates whether or not it has been contacted by the sterilant for a time and at a temperature sufficient to sterilize an article;
    wherein the walls of the solid body are impervious to the sterilant, and wherein the walls have a thickness of at least 0.3 centimeter;
  placing the sterilization process challenge device in a sterilization chamber containing the article;
  exposing the sterilization process challenge device and the article to the sterilant and at an elevated temperature; and
  determining whether or not the sterilization indicator indicates that it has been contacted by the sterilant for a time and at a temperature sufficient to sterilize the article.

In another embodiment, there is provided a kit comprising at least one sterilization process challenge device described in any one of the above embodiments or any one of the embodiments of a process challenge device described below; and a plurality of sterilization indicators for the same or different sterilization processes.

DEFINITIONS

As used herein, "impervious to the sterilant" means that the walls do not absorb or allow sterilant to pass through, except where an opening is provided to allow sterilant to enter the space defined by the walls. For example, the walls are comprised of a continuous material which is other than a porous material.

As used herein, the term "restricted" in reference to any flow of a gas or sterilant means that the time for a defined volume of the gas or sterilant to flow is increased such that the resistance of the sterilization process challenge device to sterilization conditions is increased.

As used herein, "flow restrictor" is a structure having a restricted path which causes the flow of a gas and/or flow of a sterilant to be restricted. Examples of such structures include a small-diameter opening, a porous material, a narrow tube, and combinations thereof.

As used herein, the term "sealed within the container" means that the solid body is fully contained within the container, and sterilant enters the container in order to enter the spaced defined by the walls of the solid body.

The term "comprising" and variations thereof (e.g., comprises, includes, etc.) do not have a limiting meaning where these terms appear in the description and claims.

As used herein, "a," "an," "the," "at least one," and "one or more" are used interchangeably, unless the context clearly dictates otherwise.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

Also herein, the recitations of numerical ranges by endpoints include all numbers subsumed within that range (e.g., a volume of 50 to 500 cm$^3$ includes a volume of 50, 63, 75.5, 500 cm$^3$ etc.).

The above summary of the present invention is not intended to describe each disclosed embodiment or every implementation of the present invention. The description that follows more particularly exemplifies illustrative embodiments.

BRIEF DESCRIPTIONS OF THE DRAWINGS

FIG. 4 is a perspective view of a solid body with a threaded area as a flow restrictor.

FIG. 5 is a perspective view of another embodiment of a solid body.

FIG. 5A is a cross-sectional view of the solid body of FIG. 5.

DETAILED DESCRIPTION OF ILLUSTRATIVE EMBODIMENTS OF THE INVENTION

Figure 1:
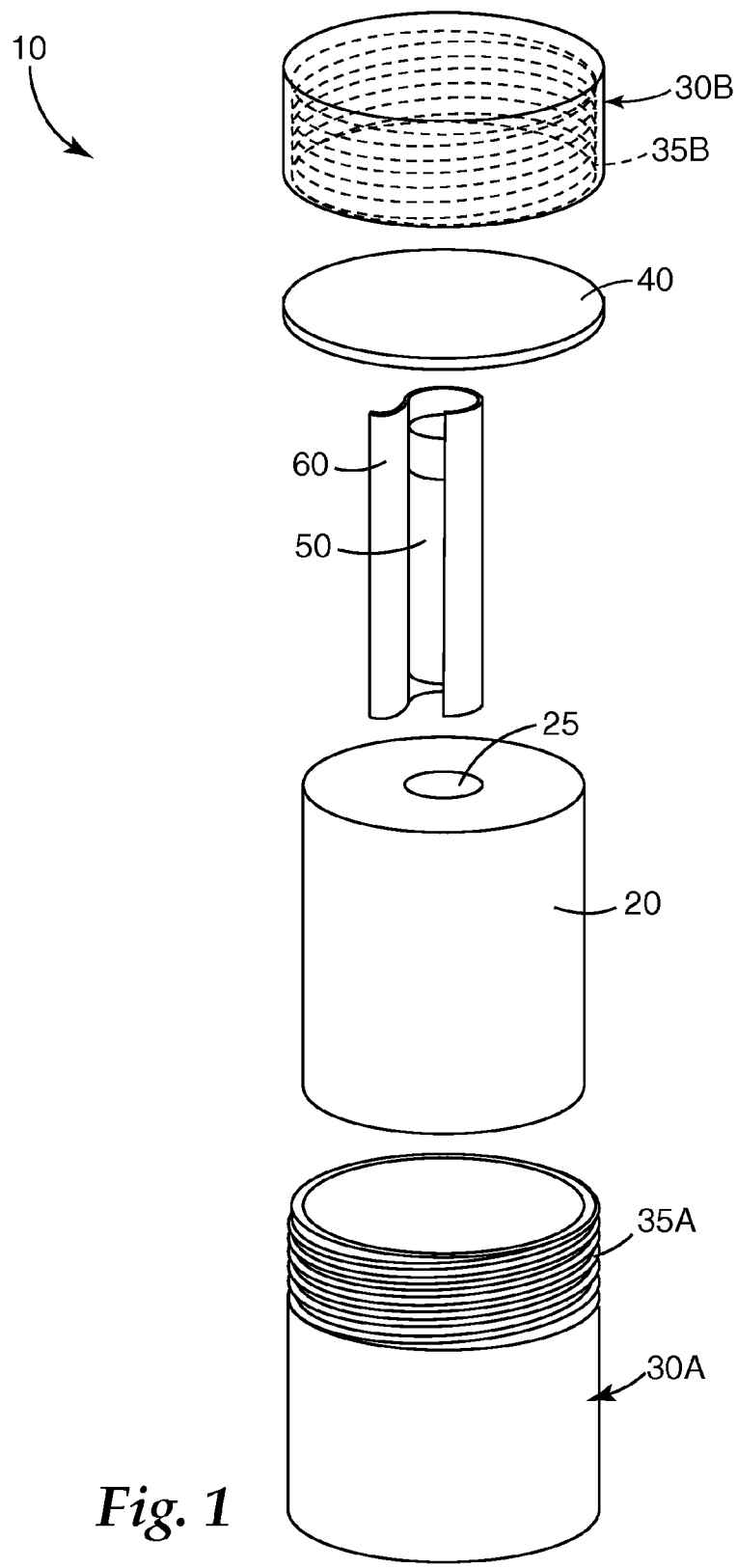
FIG. 1 is a perspective exploded view of a device according to the present invention where an optional indicator and absorbent covering around the indicator are present.

One illustrative sterilization process challenge device 10 is illustrated in FIG. 1. Solid body 20 is round with cylindrical walls, although alternative shapes can be used. The cylindrical walls define space 25, which extends entirely through solid body 20, although space 25 can extend only part way through the solid body 20. The solid body 20 fits within the illustrated container shown as a first portion of the container 30A and a second portion of the container 30B. Both 30A and 30B have threaded areas 35A and 35B, such that 30A and 30B can be associated with each other by mating the threaded areas 35A and 35B. The mated treaded areas provide a restricted path for a gas to flow out of the container and a sterilant to flow into the container.

With 30A and 30B mated, the solid body is sealed within the container along with a volume of gas of at least 5 cm$^3$. The walls comprising solid body 20 have a thickness of at least 0.3 cm. For certain embodiments, preferably the walls of the solid body 20 have a thermal diffusivity ($\alpha$) of not more than $1\times10^{-5}$ m$^2$/s at 20° C.

In FIG. 1, optional porous disc 40, which can be a fibrous material such as paper, can be used as a spacer to prevent stopping all flow out of or into the container when associating 30A with 30B. The disc 40 can also act as a flow restrictor.

An optional sterilization indicator 50 is also illustrated in FIG. 1. The sterilization process challenge device of the present invention can be provided without or with indicator 50, which is chosen to be used with sterilization conditions to be employed in a particular sterilization process. When the device is provided without the indicator 50, the indicator 50 is selected and placed in the device prior to using the device in the sterilization process. For example, for a steam sterilization process, a steam sterilization indicator is selected for indicator 50. Moreover, the indicator 50 can be chosen based upon the amount of exposure to sterilization conditions required to cause indicator 50 to indicate that the exposure has occurred. The choice of the sterilization indicator can thereby be used to increase or decrease the resistance of the sterilization process challenge device.

FIG. 1 also illustrates an optional absorbent material 60 around the indicator 50. When absorbent material 60 is present, space 25 is dimensioned to allow the indicator and absorbent material to fit within space 25. The absorbent material can absorb the condensate of a sterilant to prevent or reduce the amount of condensate that can contact the sterilization indicator, thereby preventing undesired indicator error. Furthermore, preventing condensate formation on the indicator reduces the heat gain of the indicator caused by heat transfer from the sterilant. For example, with steam sterilization, the absorbent material absorbs water which would otherwise condense on the indicator. A suitable absorbent material is cellulose or other absorbent fiber, such as absorbent paper.

When absorbent material is included with the sterilization indicator in any of the embodiments described herein, the resistance of the sterilization process challenge device can be increased compared to without the absorbent material. However, the solid body and the flow restrictor have a greater effect on the resistance.

As shown in FIG. 1, the absorbent material can extend beyond the ends of the indicator, such that when placed within space 25 and centered therein, the indicator can be retrieved from space 25 by pulling on the absorbent material.

For certain embodiments, when indicator 50 is within space 25, the distance between indicator 50 and the walls of solid body 20 is preferably less than 5 cm. For certain embodiments the distance is less than 2 cm, 1 cm, 0.75 cm, or 0.5 cm. For certain embodiments, the indicator 50 can contact the walls of the solid body 20. Preferably, the distance between the indicator 50 and the walls of the solid body 20 is sufficient to allow a layer of absorbent material between the walls and the indicator.

Figure 1A:
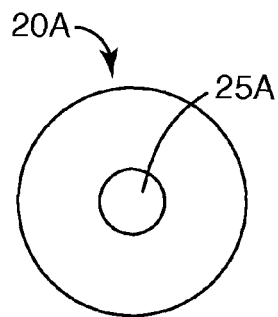
FIG. 1A is a top view of a cylindrical solid body.

FIG. 1A illustrates solid body 20A, which is a top view of solid body 20 shown in FIG. 1. Space 25A is illustrated as having a circular cross-section. However, other cross-sectional shapes, e.g., square, rectangular, oval, triangular, etc., can be used as long as the sterilization indicator fits within the space, and in certain embodiments the space contains at least 5 cm$^3$ volume of a gas. The wall thickness of solid body 20A is the radius of solid body 20A minus the radius of the cross-section of space 25A.

Figure 1B:
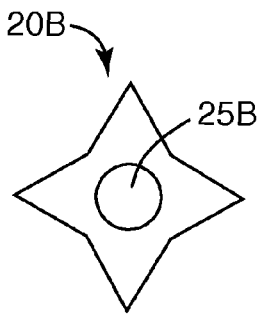
FIG. 1B is a top view of an alternatively shaped solid body.
Figure 1C:
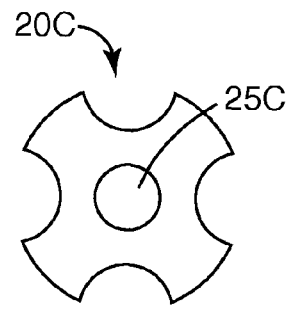
FIG. 1C is a top view of another alternatively shaped solid body.
Figure 1D:
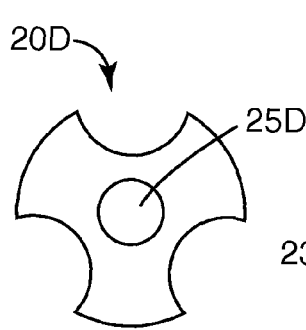
FIG. 1D is a top view of another alternatively shaped solid body.

FIGS. 1B, 1C, and 1D illustrate top views of solid bodies 20B, 20C, and 20D, which have alternative cross-sectional shapes as shown. Spaces 25B, 25C, and 25D are as described in FIG. 1A. The wall thicknesses of solid bodies 20B, 20C, and 20D vary radially from spaces 25B, 25C, and 25D. The wall thickness of each of these can be determined as a mean wall thickness. However, in certain embodiments, preferably the wall thickness is at least 0.3 cm at any location in these solid bodies.

Figure 1E:
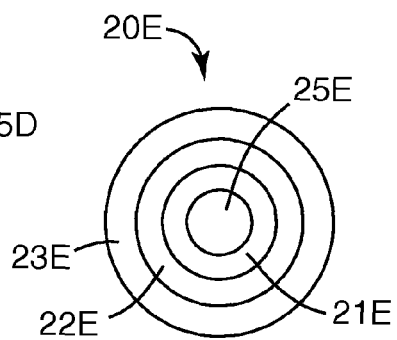
FIG. 1E is a top view of a solid body with adjustable wall thickness and/or adjustable thermal diffusivity.

FIG. 1E illustrates solid body 20E with space 25E and comprising three layers, although two layers or more than three layers can be used. Solid body 20E can be adjusted for wall thickness by removing one or two of solid body layers 21E, 22E, and 23E, and thereby decrease the resistance of the device to sterilization conditions. Although not shown, one or more additional solid body layers can be added to increase the wall thickness of solid body 20E, and thereby increase the resistance of the device to sterilization conditions. Moreover, solid body layers 21E, 22E, and 23E can have the same or different thermal diffusivities, allowing the thermal diffusivity of solid body 20E to be adjusted for a particular sterilization process. Solid body 20E and layers 21E, 22E, and 23E and space 25E are shown as circular in cross-section. However other cross-sectional shapes may be used as described above. Additionally, the thicknesses of solid body layers 21E, 22E, and 23E can be the same or different, thereby providing some additional ability to tailor the resistance of the device to sterilization conditions.

Figure 1F:
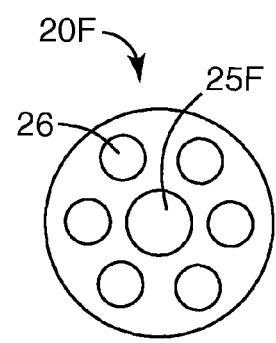
FIG. 1F is a top view of another solid body with adjustable wall thickness.

FIG. 1F illustrates solid body 20F with space 25F and a plurality of spaces 26, which can be occupied by a gas and contribute to the volume of gas contained by the solid body. Alternatively, spaces 26 can be occupied by the same material as solid body 20F or one or more different materials to arrive at a desired composite thermal diffusivity and mean wall thickness. Thus solid body 20F is adjustable for wall thickness and thermal diffusivity. Solid body 20F, space 25F, and the plurality of spaces 26 are shown as circular in cross-section. However other cross-sectional shapes may be used as described above.

Figure 1G:
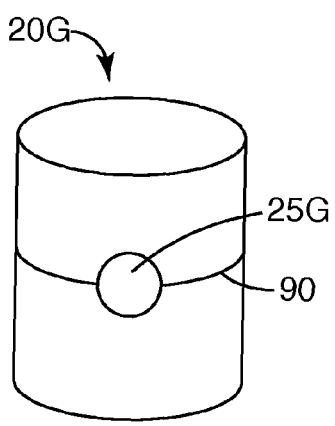
FIG. 1G is a perspective view of an alternatively configured solid body.

FIG. 1G illustrates solid body 20G with space 25G. Solid body 20G is shown with optional seam 90, such that solid body 20G comprises a top part and a bottom part. However, solid body 20G can be a single part with no seam. As a two-part solid body, 20G can be adjusted for thermal diffusivity by using a top part with one thermal diffusivity and a bottom part with a different thermal diffusivity.

Figure 2:
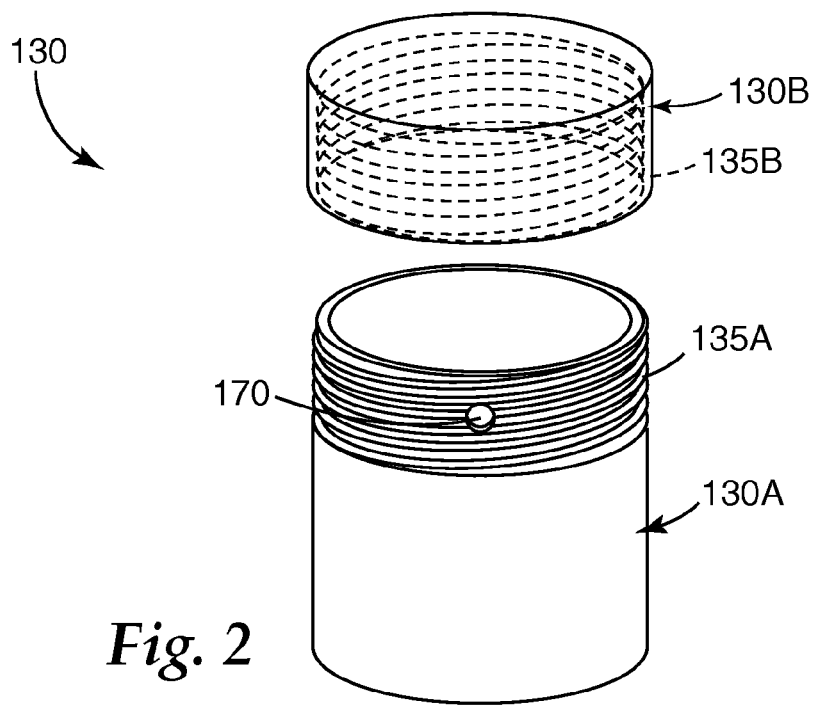
FIG. 2 is a perspective view of a container with an opening as a flow restrictor in the threaded area of the container.

FIG. 2 illustrates a container 130 with first portion 130A and second portion 130B. Both 130A and 130B have threaded areas 135A and 135B, such that 130A and 130B can be associated with each other by mating the threaded areas 135A and 135B. The mated threaded areas provide a restricted path for a gas to flow out of the container and a sterilant to flow into the container. Opening 170 is a restricted path for flow of gas and sterilant, and in combination with the mated threaded areas, opening 170 is a flow restrictor.

Figure 3:
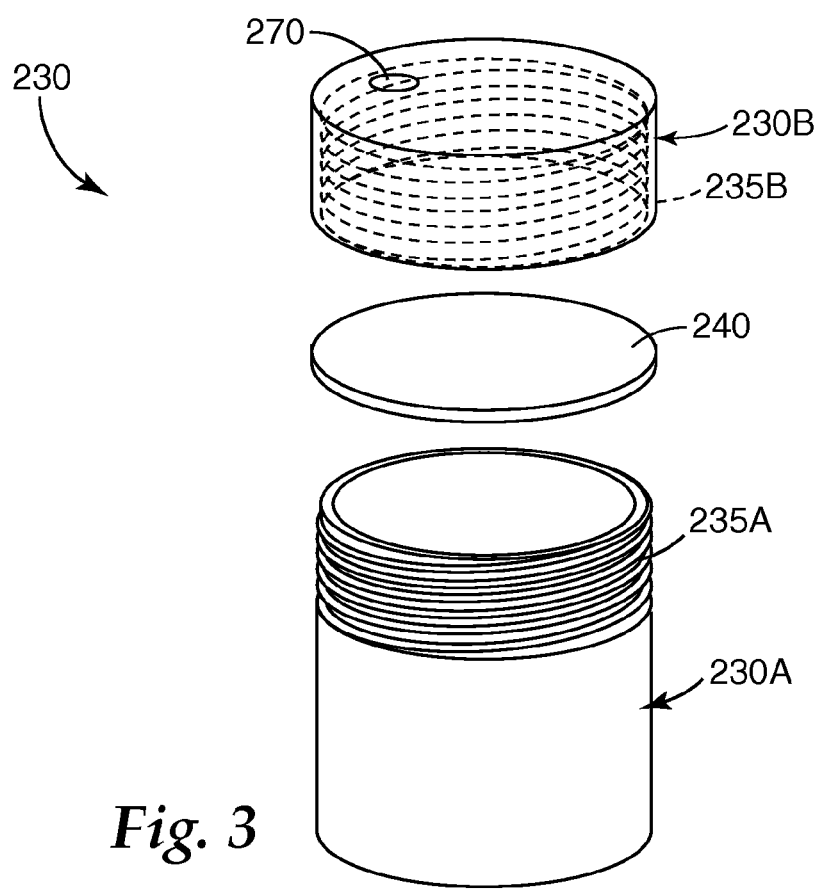
FIG. 3 is a perspective view of a container with an opening as a flow restrictor in the cap of the container and a porous disc as a further flow restrictor.

FIG. 3 illustrates a container 230 with first portion 230A and second portion 230B. Both 230A and 230B have threaded areas 235A and 235B, such that 230A and 230B can be associated with each other by mating the threaded areas 235A and 235B. The mated threaded areas can provide a restricted path for a gas to flow out of the container and a sterilant to flow into the container. Opening 270 is a restricted path for flow of gas and sterilant, and although shown on 230B, it can be located anywhere on 230A as well. Optional porous disc 240 can be included to further restrict flow of gas and sterilant through opening 270. In combination with the mated threaded areas, opening 270 and porous disc 240 are a flow restrictor. Although 230A and 230B are shown with threads for sealing container 230, other known means of sealing the container can be used such a crimping, sealing with an adhesive, use of a groove on 230B mating with a lip on 230A, and the like. One example is shown in FIG. 1 of European Patent No. 0419282.

FIG. 4 illustrates solid body 420 with space 425 and with first portion 430A and second portion 430B. Both 430A and 430B have threaded areas 435A and 435B, such that 430A and 430B can be associated with each other by mating the threaded areas 435A and 435B. The mated threaded areas can provide a restricted path for a gas to flow out of the container and a sterilant to flow into the container. The resulting flow restrictor can be adjusted for restricting the path to a greater or lesser degree by mating more or less of the threaded areas 435A and 435B. Solid body 420 can be used as the sterilization process challenge device without placing it in a container, or it can be placed in a container, such as any one described herein, to provide a sterilization process device. Solid body 420 includes an optional recessed area 480 for accepting a sterilization indicator and thereby keeping the indicator substantially centered in space 425.

FIG. 5 illustrates solid body 520 with space 525 and with first portion 527 and second portion 528, which mate together at seam 590. Seam 590 provides a restricted path for flow of a gas and the sterilant. The flow restrictor provided by seam 590 can be adjusted by changing the length of seam 590. Solid body 520 can be used as the sterilization process challenge device without placing it in a container, or it can be placed in a container, such as any one described herein, to provide a sterilization process device.

FIG. 5A illustrates solid body 520 with space 525 and with first portion 527 and second portion 528, which mate together at seam 590 in cross-section.

Figure 6:
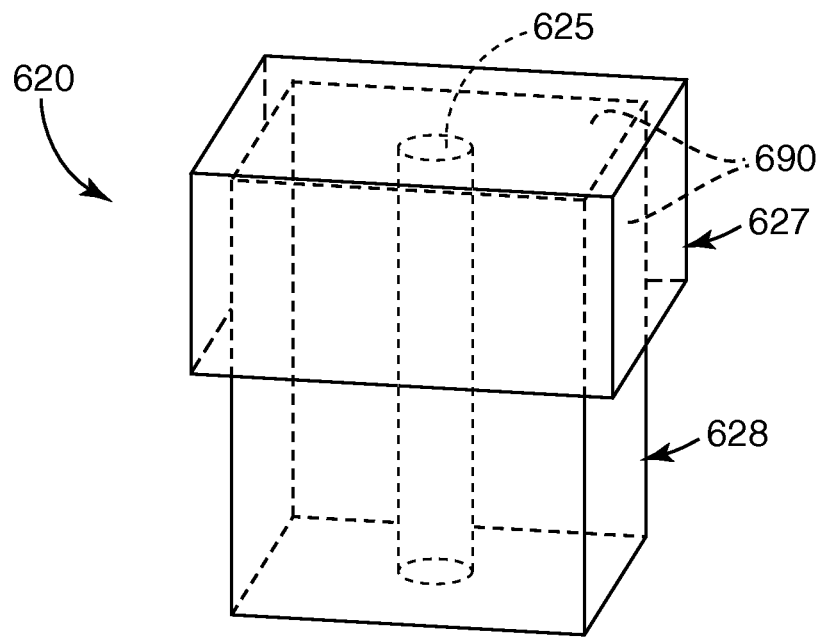
FIG. 6 is a perspective view of another embodiment of a solid body.

FIG. 6 illustrates solid body 620 with space 625 and with first portion 627 and second portion 628, which mate together at seam 690. Seam 690 provides a restricted path for flow of a gas and the sterilant. Solid body 620 can be used as the sterilization process challenge device without placing it in a container, or it can be placed in a container, such as any one described herein, to provide a sterilization process device.

Figure 7:
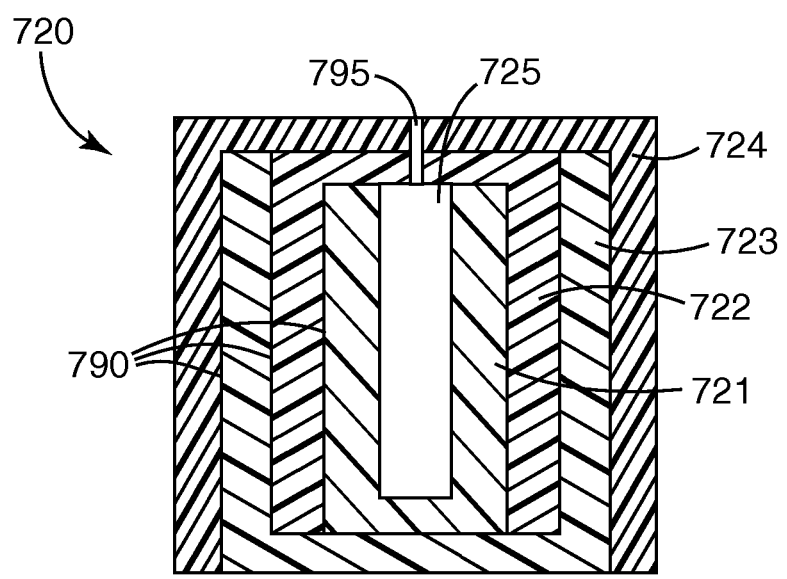
FIG. 7 is a perspective view of another embodiment of a solid body with adjustable wall thickness and/or adjustable thermal diffusivity.

FIG. 7 illustrates solid body 720 with space 725 and with solid body layers 721, 722, 723, and 724 in cross-section.

Solid body layers 721, 722, 723, and 724 mate together to form seam 790, which provides a restricted path for flow of a gas and the sterilant. Solid body 720 is shown with walls comprised of four layers, although fewer or more layers can be used. Solid body 720 can be adjusted for wall thickness by removing one, two, or three of solid body layers 721, 722, 723, and 724, and thereby decrease the resistance of the device to sterilization conditions. Although not shown, one or more additional solid body layers can be added to increase the wall thickness of solid body 720, and thereby increase the resistance of the device to sterilization conditions. Moreover, solid body layers 721, 722, 723, and 724 can have the same or different thermal diffusivities, allowing the thermal diffusivity of solid body 720 to be adjusted for a particular sterilization process. Solid body 720 and layers 721, 722, 723, and 724 and space 725 can be shaped as a cylinder, a box, or another shape, provided that layers 721, 722, 723, and 724 mate together to form seam 790. Additionally, the thicknesses of solid body layers 721, 722, 723, and 724 can be the same or different, thereby providing some additional ability to tailor or fine-tune the resistance of the device to sterilization conditions.

FIG. 7 includes an optional opening 795 which can serve as restricted path for flow of a gas or the sterilant. As shown, opening 795 goes through layers 724 and 722 directly to space 725. Alternatively, opening 795 can go through layer 724 and be off-set in layer 722 or another layer, so that flow through opening 795 must travel through seam 790 for a distance before entering space 725.

Solid body 720 can be used as the sterilization process challenge device without placing it in a container, or it can be placed in a container, such as any one described herein, to provide a sterilization process device.

Figure 8:
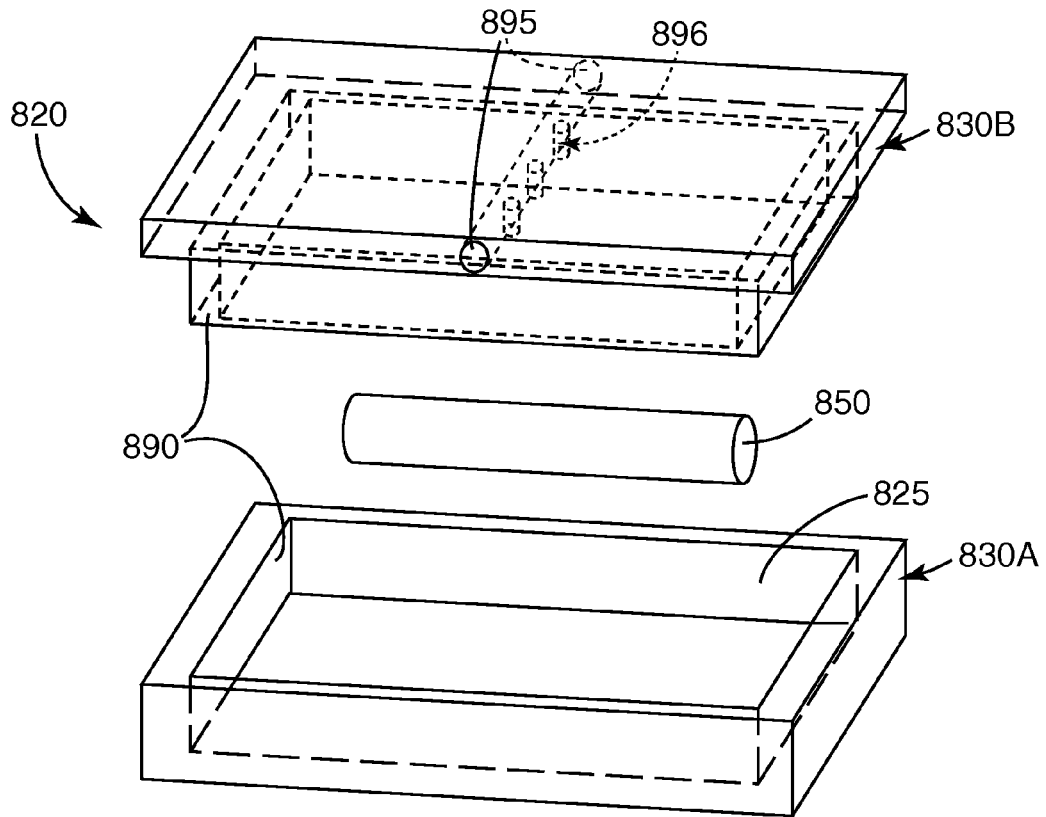
FIG. 8 is a perspective exploded view of another solid body with an optional sterilization indicator.

FIG. 8 illustrates solid body 820 with space 825 and with first portion 830A and second portion 830B, which mate together at seam 890. Seam 890 can provide a restricted path for flow of a gas and the sterilant into space 825, or alternatively 830A and 830B can be mated together with a gasket, which is not shown. Opening 895 and manifold 896 provide a restricted path for flow of a gas and the sterilant. The flow restrictor provided by opening 895 and manifold 896 can be adjusted by opening or sealing a portion of the manifold. Solid body 820 can be used as the sterilization process challenge device without placing it in a container, or it can be placed in a container, such as any one described herein, to provide a sterilization process device.

An optional sterilization indicator 850 is also illustrated in FIG. 8. The sterilization process challenge device of the present invention can be provided without or with indicator 850, which is chosen to be used with sterilization conditions to be employed in a particular sterilization process. When the device is provided without the indicator 850, the indicator 850 is selected and placed in the device prior to using the device in the sterilization process. Although not shown, indicator 850 can be covered with a porous material, such as paper or fabric. For certain embodiments, indicator 850 is sandwiched between two or more layers of a porous material. For certain embodiments, preferably the porous material absorbs sterilant condensate.

Figure 9:
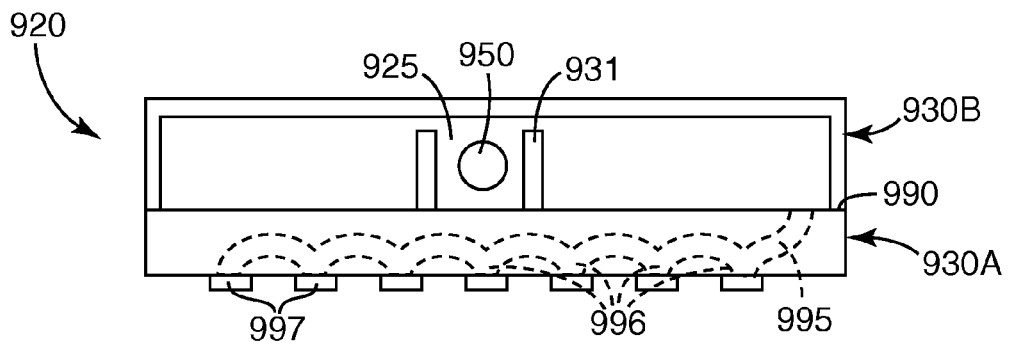
FIG. 9 is a cross-sectional view of another solid body with an adjustable path-length flow restrictor and with an optional sterilization indicator.

FIG. 9 illustrates a cross-section of solid body 920 with space 925 and with first portion 930A and second portion 930B, which mate together at seam 990. Preferably, seam 990 does not allow flow of a gas or sterilant. Second portion 930A includes a restricted path 995 for flow of a gas and the sterilant into space 925. Openings 996 are sealed with removable seals 997. The flow restrictor provided by restricted path 995 with one or more openings 996 can be adjusted by removing one or more removable seals 997.

Solid body 920 is shown with optional indicator 950 between optional baffles 931 for keeping the indicator 950 substantially centered or in a desired location within space 925.

Figure 10:
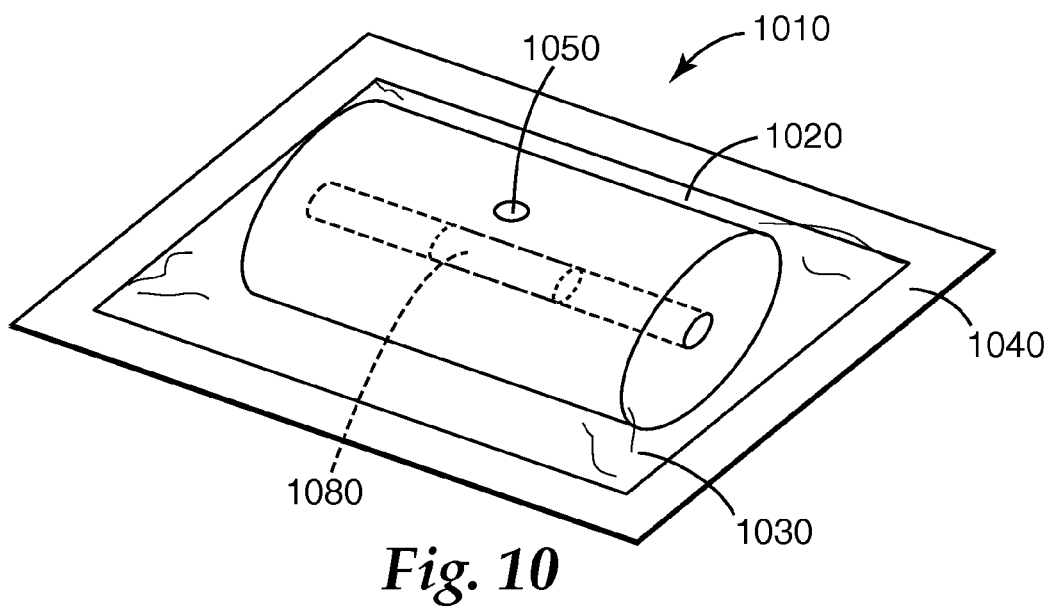
FIG. 10 is a perspective view of another embodiment of a device according to the present invention, which includes a container with flexible walls.

Sterilization process challenge device 1010 illustrated in FIG. 10 is another embodiment of a process challenge device described herein. Device 1010 includes container 1030 constructed with two sheets, each a flexible material and each forming a wall, heat sealed together at seal 1040 to define the space in which heat-transfer modulating body 1020 resides, and with opening 1050 as a flow restrictor in one of the two walls. Solid body 1020 surrounds but does not envelop process indicator 1080. Except for the opening in body 1020 through which indicator 1080 is inserted, body 1020 may be impervious to a sterilant. Body 1020 may be selected for a selected sterilization process with the walls of body 1020 being thicker and/or having a lower thermal diffusivity for greater resistance or thinner and/or having a higher thermal diffusivity for lesser resistance to a sterilization process.

Figure 11:
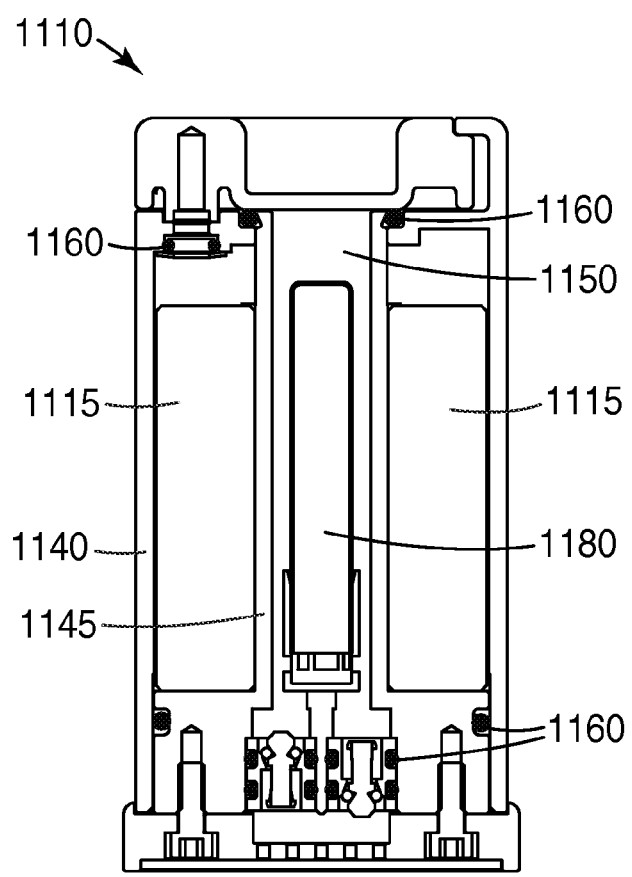
FIG. 11 is a schematic cross-section view of another embodiment of a device according to the present invention, wherein the flow restrictor is two pressure-actuating valves.

Sterilization process challenge device 1110 illustrated in FIG. 11 is another embodiment of a process challenge device described herein. Device 1110 includes a solid body 1115 positioned between walls 1145 and outer walls of container 1140. Body 1115 is illustrated as surrounding the process indicator 1180 positioned within space 1150 defined by walls 1145. For certain embodiment, alternatively, body 1115 can only partially surround indicator 1180. Seals 1160 reduce or eliminate leakage of any gas and/or liquid into or out of space 1150 and the space wherein body 1115 resides. The two pressure-actuating valves illustrated as poppet style check valves are illustrated at the base of space 1150 below indicator 1180. However, various other known valve designs may be used. One of the valves is actuated when the pressure outside of outer walls of container 1140 is higher than the pressure in space 1150. The other valve is actuated when the pressure in space 1150 is higher than outside outer walls of container 1140. The valves can be chosen to actuate at a particular pressure, for example at a pressure of 68.95 Pa (10 psi). The valves can be chosen to actuate at the same pressure or at a different pressure. One of the two pressure-actuating valves regulates entrance of a sterilant into space 1150, and the other pressure-actuating valve regulates exiting of a gas and/or a liquid out of space 1150. By selecting or adjusting the valves to actuate at a sufficiently high pressure or at a sufficiently low pressure, a process indicator contained within space 1150 will require a greater or less amount of time, respectively, in a sterilization process to indicate that sterilizing conditions have been achieved. In one alternative, for certain embodiments, a combination valve may be used. Such a valve can be used to regulate both entrance of a sterilant and exiting of a gas and/or liquid.

As indicated above, the space defined by the walls of the solid body contain a volume of gas of at least 5 $cm^3$. For certain embodiments, including any one of the above embodiments of the solid body, the volume of gas contained within the space defined by the walls of the solid body is at least 10, 25, or 50 $cm^3$. For certain embodiments, including any one of the above embodiments of the solid body, the volume of gas contained within the space defined by the walls of the solid body is not more 1000 $cm^3$, 500 $cm^3$, 250 $cm^3$, 125 $cm^3$, or 75 $cm^3$.

As indicated above, when a solid body is sealed within a container, a volume of gas of at least 5 $cm^3$ is included within the container as well. For certain embodiments, including any one of the above embodiments where a solid body is sealed within a container, the volume of gas included within the container is at least 10, 25, or 50 cm³. For certain embodiments, including any one of the above embodiments where a solid body is sealed within a container, the volume of gas included within the container is not more 1000 cm³, 500 cm³, 250 cm³, 125 cm³, or 75 cm³. For certain embodiments, the volume of gas within the container includes any volume of gas contained within the space defined by the walls of the solid body. For certain embodiments, the volume of gas within the container is in addition to any volume of gas contained within the space defined by the walls of the solid body.

As indicated above, the walls comprising any one of the solid bodies described herein have a thickness of at least 0.3 cm. For certain embodiments, including any one of the above embodiments, the thickness is preferably at least about 0.5 cm. For certain of these embodiments, the thickness is at least 0.6 cm, 0.75 cm, 1 cm, 1.25 cm, or 2.5 cm. For certain embodiments, the thickness is at most 10 cm or 5 cm.

For certain embodiments, the walls comprising any one of the solid bodies described herein have a thermal diffusivity ($\alpha$) of not more than $1\times10^{-5}$ m²/s at 20° C. Suitable materials for the walls of the solid body include, for example, stainless steel ($\alpha$=0.405×10⁻⁵ m²/s), polypropylene, DELRIN® acetal resin, nylon ($\alpha$=1.3×10⁻⁷ m²/s), polyester, polycarbonate, polytetrafluoroethylene ($\alpha$=1.1×10⁻⁷ m²/s), and the like. For certain of these embodiments, the thermal diffusivity is not more than $5\times10^{-7}$ m²/s at 20° C. For certain of these embodiments, the thermal diffusivity is not more than $2\times10^{-7}$ m²/s at 20° C. The thermal diffusivity of the material indicates how rapidly the material adjusts its temperature to that of its surroundings. For example, a material with a relatively low thermal diffusivity heats up more slowly than a material with a higher thermal diffusivity in an environment at an elevated temperature, such as a sterilization chamber. Thermal diffusivity is used in heat transfer analysis and is the ratio of thermal conductivity to volumetric heat capacity as follows:

$$\alpha = \kappa/\rho C_p$$

where $\kappa$ is thermal conductivity (W/mK), $\rho$ is density (kg/m³), and $C_p$ is specific heat capacity (J/kgK). Thus, using these parameters, a suitable material or combination of materials for the walls of the solid body can be chosen to achieve a desired resistance to sterilization conditions used in a sterilization process. For example, a material with a particular thermal diffusivity can be used for the walls of the solid body, or the walls of the solid body can be comprised of two or more layers, where at least two of the layers have different thermal diffusivities, to provide walls with a composite thermal diffusivity.

Opening such as 170 in FIG. 2, 270 in FIG. 3, 795 in FIG. 7, 895 in FIG. 8, and 996 in FIG. 9 are a flow restrictor or a portion of a flow restrictor. Such openings are small. For certain embodiments, including any one of the above embodiments that includes an opening for flow of a gas or sterilant, the opening has a diameter of not more than 0.02 cm. For certain of these embodiments, the diameter is not more than 0.20 cm or 0.40 cm. For certain of these embodiment, the diameter is at least 0.01 cm or 0.10 cm.

Sterilization indicators which can be used in the sterilization process challenge device described herein are known and include biological indicators and chemical indicators. Examples of biological indicators include ATTEST™ 1292 Rapid Biological Indicators (available from 3M Company, St. Paul, Minn.) and those described in U.S. Pat. No. 6,623,955 can be used. Examples of chemical indicators include COM-PLY™ STERIGAGE™ 1243 Steam Chemical Integrator (available from 3M Company) and those described in U.S. Pat. No. 5,916,816 can be used.

As indicated above, the sterilization indicator can be chosen to increase or decrease the resistance of the sterilization process challenge device to sterilization conditions. Chemical indicators can be chosen with different stated values (i.e., time, temperature, or sterilant gas concentration conditions for which they show a pass result). Stated values are defined in ANSI/AAMI/ISO 11140-1:2005, Sterilization of health care products—Chemical indicators. Biological indicators can be chosen with different resistance values (i.e., spore population, D-value, or Z-value) as described, for example, in ANSI/AAMI/ISO 11138-1:2006, Sterilization of health care products—Biological indicators.

The following is a list of exemplary embodiments of the present invention.

1. A sterilization process challenge device comprising:
   a solid body comprised of walls which define a space, wherein the space can fully contain a sterilization indicator and a volume of gas of at least 5 cubic centimeters and not more than 1000 cubic centimeters;
   a flow restrictor associated with the solid body such that any flow of the gas out of the space and any flow of a sterilant into the space is restricted;
   wherein the sterilization indicator indicates whether or not it has been contacted by the sterilant for a time and at a temperature sufficient to sterilize an article;
   wherein the walls of the solid body are impervious to the sterilant, and wherein the walls have a thickness of at least 0.3 centimeter.

2. The device of embodiment 1, further comprising a container, wherein the solid body is sealed within the container, the flow restrictor is attached to or is part of the container, and any gas flow out of and any sterilant flow into the container are restricted by the flow restrictor.

3. The device of embodiment 2, wherein a volume of gas of at least 5 cubic centimeters is contained within the container in addition to the volume of gas contained in the space defined by the walls of the solid body.

4. A sterilization process challenge device comprising:
   a solid body comprised of walls which define a space, wherein the space can fully contain a sterilization indicator;
   a container, wherein the solid body is sealed within the container, and a volume of gas of at least 5 cubic centimeters is contained within the container;
   a flow restrictor attached to or which is part of the container such that any flow of the gas out of the container and any flow of a sterilant into the container is restricted;
   wherein the sterilization indicator indicates whether or not it has been contacted by the sterilant for a time and at a temperature sufficient to sterilize an article;
   wherein the walls of the solid body are impervious to the sterilant, and wherein the walls have a thickness of at least 0.3 centimeter.

5. The device of embodiment 3 or embodiment 4, wherein the container comprises at least one wall which is flexible.

6. The device of embodiment 5, wherein the volume of gas varies by at least 10 percent as a pressure differential varies between inside and outside the container.

7. The device of embodiment 6, wherein the volume of gas varies by at least 50 percent as the pressure differential varies between inside and outside the container.

8. A method of controlling the level of resistance to a sterilization process provided by a sterilization process challenge device, the method comprising:

providing a sterilization process challenge device comprising:
    a solid body comprised of walls which define a space, wherein the space can fully contain a sterilization indicator and a volume of gas of at least 5 cubic centimeters;
    a flow restrictor associated with the solid body such that any flow of the gas out of the space and any flow of a sterilant into the space is restricted;
    wherein the sterilization indicator indicates whether or not it has been contacted by the sterilant for a time and at a temperature sufficient to sterilize an article;
    wherein the walls of the solid body are impervious to the sterilant, and wherein the walls have a thickness of at least 0.3 centimeter; and
    adjusting the sterilization process challenge device to provide a targeted level of resistance to a sterilization process; wherein adjusting comprises a step selected from the group consisting of:
        adjusting the thickness of the walls,
        adjusting the thermal diffusivity of the solid body,
        adjusting the volume of the gas,
        adjusting the flow restrictor to increase or decrease the flow of the gas out of the space and the flow of the sterilant gas into the space defined by the walls of the solid body, and a combination thereof 9. A method of controlling the level of resistance to a sterilization process provided by a sterilization process challenge device, the method comprising:
providing a sterilization process challenge device comprising:
    a solid body comprised of walls which define a space, wherein the space can fully contain a sterilization indicator;
    a container, wherein the solid body is sealed within the container, and a volume of gas of at least 5 cubic centimeters is contained within the container;
    a flow restrictor attached to or which is part of the container such that any flow of the gas out of the container and any flow of a sterilant into the container is restricted;
    wherein the sterilization indicator indicates whether or not it has been contacted by the sterilant for a time and at a temperature sufficient to sterilize an article;
    wherein the walls of the solid body are impervious to the sterilant, and wherein the walls have a thickness of at least 0.3 centimeter; and
    adjusting the sterilization process challenge device to provide a targeted level of resistance to a sterilization process; wherein adjusting comprises a step selected from the group consisting of:
        adjusting the thickness of the walls,
        adjusting the thermal diffusivity of the solid body,
        adjusting the volume of the gas,
        adjusting the flow restrictor to increase or decrease the flow of the gas out of the space and the flow of the sterilant gas into the space defined by the walls of the solid body, and a combination thereof 10. The method of embodiment 8, wherein a sterilant condensate forms on the solid body when sterilant flows into the space defined by the walls of the solid body.

11. The method of embodiment 9, wherein a sterilant condensate forms on the solid body when sterilant flows into the container.

12. The method of embodiment 10 or embodiment 11, further comprising modifying the sterilization process challenge device by preventing at least a portion of the sterilant gas condensate from contacting the sterilization indicator.

13. A method of determining the effectiveness of a sterilization process for sterilizing an article, the method comprising:
providing a sterilization process challenge device comprising:
    a solid body comprised of walls which define a space, wherein the space fully contains a sterilization indicator and a volume of gas of at least 5 cubic centimeters;
    a flow restrictor associated with the solid body such that any flow of the gas out of the space and any flow of a sterilant into the space is restricted;
    wherein the sterilization indicator indicates whether or not it has been contacted by the sterilant for a time and at a temperature sufficient to sterilize an article;
    wherein the walls of the solid body are impervious to the sterilant, and wherein the walls have a thickness of at least 0.3 centimeter;
placing the sterilization process challenge device in a sterilization chamber containing the article;
exposing the sterilization process challenge device and the article to the sterilant and to an elevated temperature; and
determining whether or not the sterilization indicator indicates that it has been contacted by the sterilant for a time and at a temperature sufficient to sterilize the article.

14. A method of determining the effectiveness of a sterilization process for sterilizing an article, the method comprising:
providing a sterilization process challenge device comprising:
    a solid body comprised of walls which define a space, wherein the space fully contains a sterilization indicator;
    a container, wherein the solid body is sealed within the container, and a volume of gas of at least 5 cubic centimeters is contained within the container;
    a flow restrictor attached to or which is part of the container such that any flow of the gas out of the container and any flow of a sterilant into the container is restricted;
    wherein the sterilization indicator indicates whether or not it has been contacted by the sterilant for a time and at a temperature sufficient to sterilize an article;
    wherein the walls of the solid body are impervious to the sterilant, and wherein the walls have a thickness of at least 0.3 centimeter;
placing the sterilization process challenge device in a sterilization chamber containing the article;
exposing the sterilization process challenge device and the article to the sterilant and at an elevated temperature; and
determining whether or not the sterilization indicator indicates that it has been contacted by the sterilant for a time and at a temperature sufficient to sterilize the article.

15. The method of embodiment 13 or embodiment 14, further comprising placing the sterilization indicator into the solid body such that the space defined by the walls of the solid body fully contains the sterilization indicator.

16. The method of any one of embodiments 9, 14, and 15, wherein the container comprises at least one wall which is flexible.

17. The device of embodiment 16, wherein the volume of gas varies by at least 10 percent as a pressure differential varies between inside and outside the container.

18. The device of embodiment 17, wherein the volume of gas varies by at least 50 percent as the pressure differential varies between inside and outside the container.

19. A kit comprising at least one sterilization process challenge device of any one of embodiments 1 through 7; and a plurality of sterilization indicators for the same or different sterilization processes.

20. The kit of embodiment 19, further comprising at least one solid body in addition to the solid body of the at least one sterilization process challenge device.

21. The kit of embodiment 20, wherein the at least one solid body is a plurality of solid bodies having the same or different thermal diffusivities and the same or different wall thicknesses.

22. The kit of any one of embodiments 19, 20, and 21, wherein the thickness of the walls comprising the solid body is adjustable.

23. The kit of embodiment 22, wherein the thickness is adjustable by adding or removing at least one wall layer, wherein the at least one wall layer nests with another wall layer after being added or prior to being removed, to provide the thickness of the walls comprising the solid body.

24. The kit of any one of embodiments 19 through 23 except as dependent on embodiment 1, further comprising a plurality of containers of the same or different sizes.

25. The device of any one of embodiments 1 through 7, or the method of any one of embodiments 8 through 11, or the kit of any one of embodiments 19 through 24, wherein a sterilization indicator is fully contained in the space defined by the walls of the solid body.

26. The device of any one of embodiments 1 through 7 and 25, or the method of any one of embodiments 8 through 15 and 25, or the kit of any one of embodiments 19 through 25, wherein the sterilization indicator is selected, in combination with the sterilization process challenge device, to provide a targeted level of resistance to a sterilization process.

27. The device of any one of embodiments 1 through 7, 25, and 26, or the method of any one of embodiments 8 through 15, 25, and 26, or the kit of any one of embodiments 19 through 26, wherein the indicator is a steam sterilization indicator and the sterilant is steam.

28. The device of any one of embodiments 1 through 7, 25, 26, and 27, or the method of any one of embodiments 8 through 15, 25, 26, and 27, or the kit of any one of embodiments 19 through 27, wherein a layer of material, which absorbs a condensate of the sterilant, separates the sterilization indicator and the walls of the solid body.

29. The device of any one of embodiments 1 through 7 and 25 through 28, or the method of any one of embodiments 8 through 15 and 25 through 28, or the kit of any one of embodiments 19 through 28, wherein the sterilization indicator and the walls of the solid body are separated by a distance of not more than 2 centimeters.

30. The device of any one of embodiments 1 through 7 and 25 through 29, or the method of any one of embodiments 8 through 15 and 25 through 29, or the kit of any one of embodiments 19 through 29, wherein the solid body has a thermal diffusivity of not more than $1\times10^{-5}$ m$^2$/s at 20° C.

31. The device of embodiment 30, or the method of embodiment 30, or the kit of embodiment 30, wherein the thermal diffusivity is not more than $5\times10^{-7}$ m$^2$/s at 20° C.

32. The device of any one of embodiments 1 through 7 and 25 through 31 or the method of any one of embodiments 8 through 15 and 25 through 31, wherein the thickness of the walls of the solid body is adjustable.

33. The device of any one of embodiments 1 through 7 and 25 through 32, or the method of any one of embodiments 8 through 15 and 25 through 32, or the kit of any one of embodiments 19 through 31, wherein the walls of the solid body are comprised of more than one layer, wherein the thermal diffusivity of each layer is the same or different.

34. The device of embodiment 33, or the method of embodiment 33, or the kit of embodiment 33, wherein the thermal diffusivity of the solid body can be adjusted by adding or removing at least one layer that has a different thermal diffusivity than at least one layer of the solid body before adding or after removing the at least one added or removed layer.

35. The device of any one of embodiments 3, 4, and 25 through 34, except as dependent on embodiment 1 or embodiment 2, or the method of any one of embodiments 8 through 15, and 25 through 34, except as dependent on embodiment 1 or embodiment 2, or the kit of any one of embodiments 19 through 31, 33, and 34 except as dependent on embodiment 1 or embodiment 2, wherein the volume of gas contained within the container is 50 to 500 cubic centimeters.

36. The device of any one of embodiments 1 through 7 and 25 through 35, or the method of any one of embodiments 8 through 15 and 25 through 35, or the kit of any one of embodiments 19 through 31, 33, 34, and 35, wherein the flow restrictor comprises at least one pressure-actuated valve.

37. The device of any one of embodiments 1 through 7 and 25 through 36, or the method of any one of embodiments 8 through 15 and 25 through 36, or the kit of any one of embodiments 19 through 31, and 33 through 36, wherein the at least one pressure-actuating valve is a combination valve.

38. The device of any one of embodiments 1 through 7 and 25 through 37, or the method of any one of embodiments 8 through 15 and 25 through 37, or the kit of any one of embodiments 19 through 31, and 33 through 37, wherein the at least one pressure-actuating valve is actuated when there is a pressure difference across the valve.

39. The device of any one of embodiments 1 through 7 and 25 through 37, or the method of any one of embodiments 8 through 15 and 25 through 37, or the kit of any one of embodiments 19 through 31, and 33 through 37, wherein the at least one pressure-actuating valve is at least two pressure-actuating valves.

40. The device of embodiment 39, the method of embodiment 39, or the kit of embodiment 39, wherein the at least two pressure-actuating valves are each independently actuated when there is a pressure difference across the valve.

41. The device of embodiment 39, the method of embodiment 39, or the kit of embodiment 39, wherein a first pressure-actuating valve regulates a sterilant flow, and a second pressure-actuating valve regulates a gas and/or a liquid flow in a direction opposite the sterilant flow.

42. The device of embodiment 41, the method of embodiment 41, or the kit of embodiment 41, wherein the first pressure-actuating valve and the second pressure-actuating valve are each independently actuated when there is a pressure difference across the valve.

43. The device of any one of embodiments 38, 40, and 42, the method of any one of embodiments 38, 40, and 42, or the kit of any one of embodiments 38, 40, and 42, wherein the pressure difference at which at least one pressure-actuating valve is actuated can be adjusted.

44. The device of any one of embodiments 38, 40, 42, and 43, the method of any one of embodiments 38, 40, 42, and 43, or the kit of any one of embodiments 38, 40, 42, and 43, wherein the pressure difference is at least 6.895 kPa (1 psi).

45. The device of any one of embodiments 38, 40, 42, 43, and 44, the method of any one of embodiments 38, 40, 42, 43, and 44, or the kit of any one of embodiments 38, 40, 42, 43, and 44, wherein the pressure difference is not more than 345 kPa (50 psi).

46. The device of embodiment 45, the kit of embodiment 45, or the method of embodiment 45, wherein the pressure difference is not more than 172.4 kPa (25 psi).

Objects and advantages of this invention are further illustrated by the following examples, but the particular materials and amounts thereof recited in these examples, as well as other conditions and details, should not be construed to unduly limit this invention.

EXAMPLES

Example 1

The ATTEST™ 1292 Rapid Biological Indicators (AT-TEST BIs) and COMPLY™ STERIGAGE™ 1243 Steam Chemical Integrator (STERIGAGE), both available from 3M Company, St. Paul, Minn., were placed inside machined DELRIN® acetal resin solid bodies of different sizes and shapes. See FIGS. 1A, 1C, and 1D. DELRIN® acetal resin is available from E.I. du Pont de Nemours and Company, Wilmington, Del. The DELRIN® acetal resin inserts were placed inside 138 cm³ (4.6 ounce) aluminum screw cap cans such as shown in FIG. 1. The cans are commercially available from Elemental Container, Inc. Union, N.J. Three paper liners, shown as porous disc 40 in FIG. 1, were placed under the cap to provide a tortuous path sterilant access between the cap and the can body threads. The paper liners were made of a blotter paper with an average caliper of 0.051-0.056 cm (20-22 mils), an average porosity of 10 to 20 sec/100 cm³ and a basis weight (43.18 cm×55.88 cm (17 inches×22 inches)/500 sheets) of 40-44.5 kg (88-98 lbs). The paper is commercially available from Monadnock Paper Mills, Inc. Bennington, N.H. The complete assembly is illustrated in FIG. 1 except that three porous discs 40 rather than one were used, and no absorbent material 60 was used.

The devices were exposed in a 132° C. (270° F.) 4 pulse pre-vacuum sterilizer, AMSCO® Eagle Model 3013 Sterilizer, Steris Corporation, Mentor, Ohio. The cans were exposed in a vertical position with the cap upright for 2, 4, 6, 8 and 10 minutes. The vacuum and pressure pulse for each cycle used a vacuum level of 25.4 cm (10 inches) of mercury (in Hg) and a pressure pulse of 0.2 MPa (16 psig) (pounds per square inch gauge).

After exposure, the STERIGAGE chemical integrators were read to determine if the moving front indicator dye had moved into the Reject or Accept region of the indicator. Dye in the reject region indicates a sterilization failure. The ATTEST BIs were activated by crushing the inner ampules and incubating the indicators in the ATTEST™ Model 290 Autoreaders, 3M Company, St. Paul, Minn. which detects the fluorescence caused by the enzymatic breakdown of an enzyme substrate in the growth medium. After 3 hours of incubation, the Autoreader activates a green light indicating an acceptable sterilization cycle or a red light is activated to indicate a fluorescent positive indicator and a sterilization cycle failure. The indicators continued incubating for a total of 48 hours at 60° C. to allow surviving spores to grow and cause a visual color change in the growth medium from purple to yellow. The color change to yellow indicates a sterilization failure.

The numbers of indicators detecting a sterilization failure are shown in Table 1. Three STERIGAGE and three ATTEST BIs were tested in each device configuration listed in the table.

TABLE 1

|  | 2 Min. | | | 4 Min. | | | 6 Min. | | | 8 Min. | | | 10 Min. | | |
| --- | --- | --- | --- | --- | --- | --- | --- | --- | --- | --- | --- | --- | --- | --- | --- |
| SB | SG | 3 h | G | SG | 3 h | G | SG | 3 h | G | SG | 3 h | G | SG | 3 h | G |
| Full | 3 | 3 | 1 | 3 | 3 | 1 | 1 | 3 | 0 | 1 | 3 | 0 | 0 | 0 | 0 |
| R-60 | 3 | 3 | 1 | 3 | 3 | 1 | 0 | 3 | 1 | 0 | 0 | 0 | 0 | 0 | 0 |
| R-50 | 3 | 3 | 1 | 2 | 2 | 1 | 0 | 2 | 0 | 0 | 2 | 0 | 0 | 0 | 0 |
| Full-L | 3 | 3 | 0 | 1 | 2 | 1 | 2 | 2 | 0 | 0 | 0 | 0 | 1 | 0 | 0 |
| R-60-L | 3 | 3 | 0 | 1 | 2 | 0 | 0 | 3 | 0 | 0 | 0 | 0 | 0 | 1 | 0 |
| R-50-L | 2 | 3 | 0 | 1 | 0 | 0 | 0 | 2 | 0 | 0 | 0 | 0 | 0 | 1 | 0 |

SB = solid body.
3 h = after 3 hours incubation.
G = growth.
SG = STERIGAGE
Full and Full-L = solid body of FIG. 1A with outside diameter of 4.14 cm, diameter of space of 1.27 cm, and height of solid body of 5.74 cm for Full and 7.62 cm for Full-L.
R-60, R-60-L, R-50, and R-50-L = solid bodies of FIG. 1D (R-60 and R-60-L) and 1C (R-50 and R-50-L) with maximum outside diameter of 4.14 cm, minimum wall thickness of 0.51 cm, and height of solid body of 5.74 cm for R-60 and R-50, and 7.62 cm for R-60-L and R-50-L.

The indicators following the exposure in the sterilizer were very wet from the condensate that collected inside the solid body. The correlation between the STERIGAGE and ATTEST results were not as good as expected, and condensate appeared to be interfering with the indicator response.

Example 2

Indicators Wrapped with an Absorbent

The ATTEST™ 1292 Rapid Biological Indicators (AT-TEST BIs) and COMPLY™ STERIGAGE™ 1243 Steam Chemical Integrator (STERIGAGE), both available from 3M Company, St. Paul, Minn., were placed inside machined DELRIN® acetal resin solid bodies of different sizes and shapes as shown in FIGS. 1A, 1C, and 1D. DELRIN® acetal resin is available from E.I. du Pont de Nemours and Company, Wilmington, Del. The same solid bodies tested in Example 1 and three additional inserts were included in the testing. The first new insert (solid body) was a machined DELRIN® acetal resin part as shown in FIG. 1D and identified as "R-80". The second insert (solid body) was a machined DELRIN® acetal resin part as shown in FIG. 1A and identified as "1-layer". The third new insert, described as "paper" consisted of a STERIGAGE and an ATTEST BI rolled in a paper towel plus two additional pieces of paper towel approximately 28 by 13 cm (11 by 5.1 inches) stuffed around the indicators inside the can. The DELRIN® acetal resin inserts were placed inside 138 cm³ (4.6 ounce) aluminum screw cap cans as shown in FIG. 1 and commercially available from Elemental Container, Inc. Union, N.J. Three paper liners were placed under the cap, as in Example 1. In addition to new inserts used in this example, the STERIGAGE and ATTEST were rolled up together inside an absorbent paper towel approximately 14 by 13 cm (5.5 by 5.1 inches). The paper towel is commercially available as KLEENEX® PRE- MIERE kitchen roll towel, Kimberly-Clark, Roswell, Ga. FIG. 1 illustrates the assembly using the absorbent material 60.

The devices were exposed in a 132° C. (270° F.) 4 pulse pre-vacuum sterilizer, AMSCO® Eagle Model 3013 Sterilizer, Steris Corporation, Mentor, Ohio. The cans were exposed in a vertical position with the cap upright for 2, 4, 6, 8, 10 and 12 minutes. The vacuum and pressure pulse for each cycle used a vacuum level of 25.4 cm of mercury (10 inches Hg) and a pressure pulse of 0.2 MPa (16 psig).

The numbers of indicators detecting a sterilization failure are shown in Table 2. Three STERIGAGE and three ATTEST BIs were tested in each device configuration listed in the table.

TABLE 2

| SB | 2 Min. | | | 4 Min. | | | 6 Min. | | | 8 Min. | | | 10 Min. | | | 12 Min. | | |
|---|---|---|---|---|---|---|---|---|---|---|---|---|---|---|---|---|---|---|
|  | SG | 3 h | G | SG | 3 h | G | SG | 3 h | G | SG | 3 h | G | SG | 3 h | G | SG | 3 h | G |
| Full | 3 | 3 | 3 | 3 | 3 | 3 | 3 | 3 | 3 | 3 | 3 | 3 | 3 | 3 | 3 | 3 | 3 | 3 |
| R-80 | 3 | 3 | 3 | 3 | 3 | 3 | 3 | 3 | 3 | 3 | 3 | 3 | 3 | 3 | 2 | 2 | 3 | 2 |
| R-60 | 3 | 3 | 3 | 3 | 3 | 3 | 3 | 3 | 3 | 3 | 3 | 3 | 1 | 3 | 1 | 0 | 1 | 0 |
| R-50 | 3 | 3 | 3 | 3 | 3 | 3 | 3 | 3 | 3 | 1 | 3 | 1 | 0 | 1 | 1 | 0 | 0 | 0 |
| Full-L | 3 | 3 | 3 | 3 | 3 | 3 | 3 | 3 | 3 | 3 | 3 | 3 | 2 | 3 | 3 | 3 | 3 | 3 |
| R-80-L | 3 | 3 | 3 | 3 | 3 | 3 | 3 | 3 | 3 | 3 | 3 | 3 | 3 | 3 | 3 | 3 | 3 | 2 |
| R-60-L | 3 | 3 | 3 | 3 | 3 | 3 | 3 | 3 | 3 | 3 | 3 | 3 | 2 | 3 | 3 | 0 | 2 | 0 |
| R-50-L | 3 | 3 | 3 | 3 | 3 | 3 | 3 | 3 | 3 | 3 | 3 | 3 | 0 | 3 | 1 | 0 | 1 | 0 |
| 1-La | 3 | 3 | 3 | 3 | 3 | 3 | 3 | 3 | 3 | 3 | 3 | 3 | 1 | 3 | 3 | 0 | 0 | 0 |
| Pap | 3 | 3 | 3 | 0 | 1 | 1 | 0 | 1 | 0 | 0 | 0 | 0 | 0 | 0 | 0 | 0 | 0 | 0 |

SB = solid body.
3 h = after 3 hours incubation.
G = growth.
SG = STERIGAGE.
Full and Full-L = solid body of FIG. 1A with outside diameter of 4.14 cm, diameter of space of 1.27 cm, and height of solid body of 5.74 cm for Full and 7.62 cm for Full-L.
R-80, R-80-L, R-60, R-60-L, R-50, and R-50-L = solid bodies of FIG. 1D (R-80, R-80-L, R-60 and R-60-L) and 1C (R-50 and R-50-L) with maximum outside diameter of 4.14 cm, diameter of space of 1.27 cm, minimum wall thickness of 0.51 cm, and height of solid body of 5.74 cm for R-80, R-60 and R-50, and 7.62 cm for R-80-L, R-60-L and R-50-L.
1-La = "1-layer", solid body of FIG. 1A with outside diameter of 2.69 cm, diameter of space of 1.27 cm, and height of solid body of 6.35 cm.
Pap = "paper".

The condensate was absorbed by the paper towel wrapped around the STERIGAGE and ATTEST BIs. This significantly improved the correlation between the STERIGAGE and the fluorescence and growth results of the ATTEST BIs. Additionally, the time to inactivate, or sterilize the ATTEST BIs increased significantly. In Example 1, the ATTEST BIs were all killed after 8 minutes of exposure at 132° C. In this example, a large number of ATTEST BIs were still fluorescent and growth positive after 12 minutes of exposure. This example also illustrates how the size and shape of the insert can affect the time to inactive the indicators. As more material was added to the solid body, the time to inactive the indicator increased. The device with the "paper" insert was inactivated much faster than indicators exposed with the DELRIN® acetal resin solid bodies.

Example 3

Horizontal Position in the Sterilizer

Example 2 was repeated except the devices were exposed horizontally in the sterilizer and the exposure times were 2, 4, 6, 8, and 10 minutes.

The numbers of indicators detecting a sterilization failure are shown in Table 3. The number of devices tested in each configuration is listed in the table under "No. Tested".

TABLE 3

| SB | No. Tested | 2 min | | | 4 min | | | 6 min | | |
|---|---|---|---|---|---|---|---|---|---|---|
|  |  | SG | 3 HR | Gr. | SG | 3 HR | Gr. | SG | 3 HR | Gr. |
| Full | 3 | 3 | 3 | 3 | 3 | 3 | 3 | 3 | 3 | 2 |
| R-80 | 3 | 3 | 3 | 3 | 3 | 3 | 2 | 1 | 1 | 0 |
| R-60 | 3 | 3 | 3 | 3 | 3 | 3 | 2 | 2 | 0 | 0 |
| R-50 | 3 | 3 | 3 | 3 | 2 | 1 | 0 | 0 | 0 | 0 |
| Full-L | 2 | 2 | 2 | 2 | 2 | 2 | 2 | 2 | 2 | 2 |
| R-80-L | 2 | 2 | 2 | 2 | 2 | 2 | 2 | 2 | 2 | 2 |
| R-60-L | 2 | 2 | 2 | 2 | 2 | 2 | 2 | 2 | 2 | 2 |
| R-50-L | 2 | 2 | 2 | 2 | 2 | 2 | 2 | 1 | 0 | 0 |
| 1-layer | 3 | 3 | 3 | 3 | 3 | 3 | 1 | 1 | 1 | 0 |
| Paper | 3 | 0 | 1 | 1 | 0 | 0 | 0 | 0 | 0 | 0 |

TABLE 3-continued

| SB | No. Tested | 8 min | | | 10 min | | |
|---|---|---|---|---|---|---|---|
|  |  | SG | 3 h | G | SG | 3 h | G |
| Full | 3 | 2 | 1 | 1 | 1 | 0 | 0 |
| R-80 | 3 | 0 | 0 | 0 | 1 | 0 | 0 |
| R-60 | 3 | 0 | 0 | 0 | 0 | 0 | 0 |
| R-50 | 3 | 0 | 0 | 0 | 0 | 0 | 0 |
| Full-L | 2 | 2 | 2 | 2 | 2 | 1 | 0 |
| R-80-L | 2 | 1 | 2 | 1 | 1 | 1 | 1 |
| R-60-L | 2 | 0 | 0 | 0 | 0 | 0 | 0 |
| R-50-L | 2 | 0 | 0 | 0 | 0 | 0 | 0 |
| 1-layer | 3 | 0 | 0 | 0 | 0 | 0 | 0 |
| Paper | 3 | 0 | 0 | 0 | 0 | 0 | 0 |

SB = solid body.
3 h = after 3 hours incubation.
G = growth.
SG = STERIGAGE
Full and Full-L = solid body of FIG. 1A with outside diameter of 4.14 cm, diameter of space of 1.27 cm, and height of solid body of 5.74 cm for Full and 7.62 cm for Full-L.
R-80, R-80-L, R-60, R-60-L, R-50, and R-50-L = solid bodies of FIG. 1D (R-80, R-80-L, R-60 and R-60-L) and 1C (R-50 and R-50-L) with maximum outside diameter of 4.14 cm, diameter of space of 1.27 cm, minimum wall thickness of 0.51 cm, and height of solid body of 5.74 cm for R-80, R-60 and R-50, and 7.62 cm for R-80-L, R-60-L and R-50-L.
1-layer = solid body of FIG. 1A with outside diameter of 2.69 cm, diameter of space of 1.27 cm, and height of solid body of 6.35 cm.

Exposing the devices in the horizontal position compared to the vertical position in Example 2 reduced the time to inactivate the indicators. For example, all the indicators tested with the "Full" insert in Example 2 indicated a sterilization failure after 12 minutes of exposure when exposed in the vertical position in the sterilizer. When exposed horizontally in Example 3, all of the ATTEST BIs were inactivated and only one of the STERIGAGE indicated a sterilization failure. This example illustrates that with this device the orientation in the sterilizer is another variable that can be used to regulate the sterilization challenge.

Example 4

Sterilant Access Provide by Holes in the can Body

Devices tested in Example 2 were retested except the sterilant access in the aluminum can was provided by drilling in the threaded area of the aluminum can as shown in FIG. 2. With the cap screwed on the can, a tortuous path was created between the threads of the cap and can. The two locations of the hole were evaluated to determine if the resulting difference in length of the sterilant path had an effect on the time to inactivate the indicators. In one configuration, the hole was drilled near the top edge of the can and had an estimated path length of 34.3 cm. In the other configuration, the hole was drilled in the middle of the threads and had an estimated path length of 21.6 cm. Hole sizes of 0.2 cm and 0.41 cm diameters were also compared. The same inserts and the indicators were wrapped in the paper towel to absorb the condensate.

The devices were exposed in a 132° C. (270° F.) 4 pulse pre-vacuum sterilizer, AMSCO® Eagle Model 3013 Sterilizer, Steris Corporation, Mentor, Ohio. The cans were exposed in a horizontal position for the exposure times listed in Table 4. The vacuum and pressure pulse for each cycle used a vacuum level of 25.4 cm of mercury (10 inches Hg) and a pressure pulse of 0.2 MPa (16 psig).

The numbers of indicators detecting a sterilization failure are shown in Table 4. The number of devices tested in each configuration is listed in the table under "No. Tested". The total number of growth positives for the 2, 4, 6, 8 and 10 minute exposures and the percent positive calculated to compare the results of the hole sizes and location. The percent growth positive results are summarized in Table 5 below.

TABLE 4

Hole size 0.2 cm and Estimated Path Length 34 cm

| SB | No. Tested | 0 min SG | 3 h | G | 1 min SG | 3 h | G | 2 min SG | 3 h | G |
|---|---|---|---|---|---|---|---|---|---|---|
| Full | 3 | NT | NT | NT | 3 | 3 | 3 | 3 | 3 | 3 |
| R-80 | 3 | NT | NT | NT | NT | NT | NT | 3 | 3 | 3 |
| R-60 | 3 | NT | NT | NT | 3 | 3 | 3 | 3 | 3 | 3 |
| R-50 | 3 | NT | NT | NT | 3 | 3 | 3 | 3 | 3 | 2 |
| Full-L | 2 | NT | NT | NT | 2 | 2 | 2 | 2 | 2 | 2 |
| R-80-L | 2 | NT | NT | NT | NT | NT | NT | 2 | 2 | 2 |
| R-60-L | 2 | NT | NT | NT | 2 | 2 | 2 | 2 | 2 | 2 |
| R-50-L | 2 | NT | NT | NT | 2 | 2 | 2 | 2 | 2 | 2 |
| 1-Layer | 3 | 3 | 3 | 3 | 3 | 3 | 3 | 3 | 3 | 3 |
| Paper | 3 | 3 | 3 | 3 | 3 | 3 | 3 | 0 | 2 | 2 |
| No. Pos. | 26 | | | | | | | | | 24 |
| % Positive | | | | | | | | | | 92.3 |

| SB | No. Tested | 3 min SG | 3 h | G | 4 min SG | 3 h | G | 5 min SG | 3 h | G |
|---|---|---|---|---|---|---|---|---|---|---|
| Full | 3 | 3 | 3 | 3 | 3 | 3 | 2 | 3 | 3 | 3 |
| R-80 | 3 | NT | NT | NT | 3 | 3 | 0 | NT | NT | NT |
| R-60 | 3 | 3 | 3 | 3 | 2 | 1 | 1 | 1 | 1 | 0 |
| R-50 | 3 | 3 | 1 | 0 | 0 | 0 | 0 | 0 | 0 | 0 |
| Full-L | 2 | 2 | 2 | 2 | 2 | 2 | 2 | 2 | 2 | 2 |
| R-80-L | 2 | NT | NT | NT | 2 | 2 | 1 | NT | NT | NT |
| R-60-L | 2 | 2 | 2 | 1 | 2 | 1 | 0 | 1 | 1 | 1 |
| R-50-L | 2 | 2 | 2 | 2 | 0 | 0 | 0 | 0 | 0 | 0 |
| 1-Layer | 3 | 3 | 3 | 3 | 2 | 1 | 1 | | | |
| Paper | 3 | 0 | 0 | 0 | 0 | 0 | 0 | | | |
| No. Pos. | 26 | | | | | | 7 | | | |
| % Positive | | | | | | | 26.9 | | | |

| SB | No. Tested | 6 min SG | 3 h | G | 8 min SG | 3 h | G | 10 min SG | 3 h | G |
|---|---|---|---|---|---|---|---|---|---|---|
| Full | 3 | 3 | 3 | 3 | 1 | 1 | 0 | 2 | 2 | 2 |
| R-80 | 3 | 1 | 0 | 0 | 2 | 0 | 0 | 1 | 0 | 0 |
| R-60 | 3 | 0 | 0 | 0 | 0 | 0 | 0 | 0 | 0 | 0 |
| R-50 | 3 | 0 | 0 | 0 | 0 | 0 | 0 | 0 | 0 | 0 |
| Full-L | 2 | 2 | 2 | 2 | 2 | 2 | 2 | 2 | 2 | 2 |
| R-80-L | 2 | 2 | 2 | 1 | 2 | 0 | 0 | 2 | 1 | 0 |
| R-60-L | 2 | 2 | 1 | 1 | 0 | 0 | 0 | 0 | 0 | 0 |
| R-50-L | 2 | 0 | 0 | 0 | 0 | 0 | 0 | 0 | 0 | 0 |
| 1-Layer | 3 | | | | | | | | | |
| Paper | 3 | | | | | | | | | |
| No. Pos. | 26 | | | 7 | | | 2 | | | 4 |
| % Positive | | | | 35 | | | 10 | | | 20 |

Hole size 0.2 cm and Estimated Path Length 21.6 cm

| SB | No. Tested | 2 min SG | 3 h | G | 4 min SG | 3 h | G | 6 min SG | 3 h | G |
|---|---|---|---|---|---|---|---|---|---|---|
| Full | 3 | 3 | 3 | 3 | 3 | 3 | 3 | 2 | 2 | 2 |
| R-80 | 3 | 3 | 3 | 3 | 3 | 1 | 0 | 2 | 0 | 0 |
| R-60 | 3 | 3 | 3 | 3 | 3 | 0 | 0 | 0 | 0 | 0 |
| R-50 | 3 | 3 | 3 | 2 | 0 | 0 | 0 | 0 | 0 | 0 |
| Full-L | 2 | 2 | 2 | 2 | 2 | 2 | 2 | 2 | 2 | 2 |
| R-80-L | 2 | 2 | 2 | 2 | 2 | 2 | 2 | 2 | 2 | 2 |
| R-60-L | 2 | 2 | 2 | 2 | 2 | 2 | 0 | 2 | 0 | 0 |
| R-50-L | 2 | 2 | 2 | 2 | 2 | 2 | 0 | 0 | 0 | 0 |
| 1-Layer | 3 | 3 | 3 | 3 | 3 | 2 | 1 | 0 | 0 | 0 |
| Paper | 3 | 0 | 0 | 0 | 0 | 0 | 0 | 0 | 0 | 0 |
| No. Pos. | 26 | | | 22 | | | 8 | | | 6 |
| % Positive | | | | 84.6 | | | 30.8 | | | 23.1 |

| SB | No. Tested | 8 min SG | 3 h | G | 10 min SG | 3 h | G |
|---|---|---|---|---|---|---|---|
| Full | 3 | 2 | 2 | 2 | 2 | 0 | 0 |
| R-80 | 3 | 0 | 0 | 0 | 0 | 0 | 0 |
| R-60 | 3 | 0 | 0 | 0 | 0 | 0 | 0 |
| R-50 | 3 | 0 | 0 | 0 | 0 | 0 | 0 |
| Full-L | 2 | 2 | 2 | 2 | 2 | 2 | 2 |
| R-80-L | 2 | 1 | 0 | 0 | 0 | 0 | 0 |
| R-60-L | 2 | 0 | 0 | 0 | 0 | 0 | 0 |
| R-50-L | 2 | 0 | 0 | 0 | 0 | 0 | 0 |
| 1-Layer | 3 | 0 | 0 | 0 | 0 | 0 | 0 |
| Paper | 3 | 0 | 0 | 0 | 0 | 0 | 0 |
| | | | | 4 | | | 2 |
| | | | | 15.4 | | | 7.7 |

Hole size 0.41 cm and Estimated Path Length 34 cm

| SB | No. Tested | 2 min SG | 3 h | G | 4 min SG | 3 h | G | 6 min SG | 3 h | G |
|---|---|---|---|---|---|---|---|---|---|---|
| Full | 3 | 3 | 3 | 3 | 3 | 3 | 3 | 3 | 3 | 3 |
| R-80 | 3 | 3 | 3 | 3 | 3 | 3 | 3 | 1 | 0 | 0 |
| R-60 | 3 | 3 | 3 | 3 | 3 | 1 | 1 | 0 | 0 | 0 |
| R-50 | 3 | 3 | 3 | 3 | 2 | 0 | 0 | 0 | 0 | 0 |
| Full-L | 2 | 2 | 2 | 2 | 2 | 2 | 2 | 2 | 2 | 2 |
| R-80-L | 2 | 2 | 2 | 2 | 2 | 2 | 2 | 2 | 2 | 2 |
| R-60-L | 2 | 2 | 2 | 2 | 2 | 2 | 2 | 2 | 1 | 0 |
| R-50-L | 2 | 2 | 2 | 2 | 2 | 2 | 1 | 1 | 0 | 0 |
| 1-Layer | 3 | 3 | 3 | 3 | 3 | 3 | 3 | 2 | 0 | 0 |
| Paper | 3 | 0 | 0 | 0 | 0 | 0 | 0 | 0 | 0 | 0 |

TABLE 4-continued

| No. Pos. | 26 | | | 23 | | | 17 | | | 7 |
| % Positive | | | | 88.5 | | | 65.4 | | | 26.9 |

| | No. | 8 min | | | 10 min | | |
| --- | --- | --- | --- | --- | --- | --- | --- |
| SB | Tested | SG | 3 h | G | SG | 3 h | G |
| Full | 3 | 3 | 2 | 2 | 2 | 2 | 1 |
| R-80 | 3 | 1 | 0 | 0 | 0 | 0 | 0 |
| R-60 | 3 | 0 | 0 | 0 | 0 | 0 | 0 |
| R-50 | 3 | 0 | 0 | 0 | 0 | 0 | 0 |
| Full-L | 2 | 2 | 2 | 2 | 2 | 2 | 2 |
| R-80-L | 2 | 1 | 1 | 1 | 0 | 0 | 0 |
| R-60-L | 2 | 0 | 0 | 0 | 0 | 0 | 0 |
| R-50-L | 2 | 0 | 0 | 0 | 0 | 0 | 0 |
| 1-Layer | 3 | 0 | 0 | 0 | 0 | 0 | 0 |
| Paper | 3 | 0 | 0 | 0 | 0 | 0 | 0 |
| No. Pos. | 26 | | 5 | | | 3 | |
| % Positive | | | 19.2 | | | 11.5 | |

Hole size 0.41 cm and Estimated Path Length 8.5 cm

| | No. | 2 min | | | 4 min | | | 6 min | | |
| --- | --- | --- | --- | --- | --- | --- | --- | --- | --- | --- |
| SB | Tested | SG | 3 h | G | SG | 3 h | G | SG | 3 h | G |
| Full | 3 | 3 | 3 | 3 | 3 | 3 | 3 | 3 | 3 | 3 |
| R-80 | 3 | 3 | 3 | 3 | 3 | 2 | 1 | 0 | 0 | 0 |
| R-60 | 3 | 3 | 3 | 3 | 2 | 1 | 1 | 0 | 0 | 0 |
| R-50 | 3 | 3 | 3 | 3 | 2 | 0 | 0 | 0 | 0 | 0 |
| Full-L | 2 | 2 | 2 | 2 | 2 | 2 | 2 | 2 | 2 | 2 |
| R-80-L | 2 | 2 | 2 | 2 | 2 | 2 | 2 | 2 | 2 | 2 |
| R-60-L | 2 | 2 | 2 | 2 | 2 | 2 | 0 | 2 | 0 | 0 |
| R-50-L | 2 | 2 | 2 | 2 | 2 | 0 | 0 | 0 | 0 | 0 |
| 1-Layer | 3 | 3 | 3 | 3 | 2 | 2 | 0 | 0 | 0 | 0 |
| Paper | 3 | 0 | 0 | 0 | 0 | 0 | 0 | 0 | 0 | 0 |
| No. Pos. | 26 | | 23 | | | 9 | | | 7 | |
| % Positive | | | 88.5 | | | 34.6 | | | 26.9 | |

| | No. | 8 min | | | 10 min | | |
| --- | --- | --- | --- | --- | --- | --- | --- |
| SB | Tested | SG | 3 h | G | SG | 3 h | G |
| Full | 3 | 3 | 1 | 1 | 2 | 2 | 1 |
| R-80 | 3 | 0 | 0 | 0 | 0 | 0 | 0 |
| R-60 | 3 | 0 | 0 | 0 | 0 | 0 | 0 |
| R-50 | 3 | 0 | 0 | 0 | 0 | 0 | 0 |
| Full-L | 2 | 2 | 2 | 2 | 2 | 2 | 2 |
| R-80-L | 2 | 0 | 0 | 0 | 0 | 0 | 0 |
| R-60-L | 2 | 2 | 0 | 0 | 0 | 0 | 0 |
| R-50-L | 2 | 0 | 0 | 0 | 0 | 0 | 0 |
| 1-Layer | 3 | 0 | 0 | 0 | 0 | 0 | 0 |
| Paper | 3 | 0 | 0 | 0 | 0 | 0 | 0 |
| No. Pos. | 26 | | 3 | | | 3 | |
| % Positive | | | 11.5 | | | 11.5 | |

SB = solid body.
3 h = after 3 hours incubation.
G = growth.
SG = STERIGAGE
NT = Not Tested
Full and Full-L = solid body of FIG. 1A with outside diameter of 4.14 cm, diameter of space of 1.27 cm, and height of solid body of 5.74 cm for Full and 7.62 cm for Full-L.
R-80, R-80-L, R-60, R-60-L, R-50, and R-50-L = solid bodies of FIG. 1D (R-80, R-80-L, R-60 and R-60-L) and 1C (R-50 and R-50-L) with maximum outside diameter of 4.14 cm, diameter of space of 1.27 cm, minimum wall thickness of 0.51 cm, and height of solid body of 5.74 cm for R-80, R-60 and R-50, and 7.62 cm for R-80-L, R-60-L and R-50-L.
1-layer = solid body of FIG. 1A with outside diameter of 2.69 cm, diameter of space of 1.27 cm, and height of solid body of 6.35 cm.

TABLE 5

Path Length Comparison

| | | % Growth Positive | | | | |
| --- | --- | --- | --- | --- | --- | --- |
| Hole Size | Path Length | 2 min | 4 min | 6 min | 8 min | 10 min |
| 0.2 cm | 34 cm | 92.3 | 26.9 | 35 | 10 | 20 |
| 0.2 cm | 21.6 cm | 84.6 | 30.8 | 23.1 | 15.4 | 7.7 |

TABLE 5-continued

Path Length Comparison

| | | % Growth Positive | | | | |
| --- | --- | --- | --- | --- | --- | --- |
| Hole Size | Path Length | 2 min | 4 min | 6 min | 8 min | 10 min |
| 0.41 cm | 34 cm | 88.5 | 65.4 | 26.9 | 19.2 | 11.5 |
| 0.41 cm | 21.6 cm | 88.5 | 34.6 | 26.9 | 11.5 | 11.5 |

The data indicated that the size of the hole and location of the sterilant access hole did not have a significant effect on the time to inactivate the ATTEST BIs.

Example 5

Polypropylene Inserts

The ATTEST™ 1292 Rapid Biological Indicators (AT-TEST BIs) and COMPLY™ STERIGAGE™ 1243 Steam Chemical Integrator (STERIGAGE), both available from 3M Company, St. Paul, Minn., were placed inside machined polypropylene inserts of different sizes and shapes. The inserts are the same size and shape as shown in FIGS. 1A, 1C, and 1D and used in previous examples, except these inserts are machined out of polypropylene instead of DELRIN® acetal resin. The polypropylene inserts were placed inside 138 cm$^3$ (4.6 ounce) aluminum screw cap cans as in Example 1.

The STERIGAGE and ATTEST BIs were rolled up together inside an absorbent paper towel as in Example 2.

The devices were exposed in a 132° C. (270° F.) 4 pulse pre-vacuum sterilizer, AMSCO® Eagle Model 3013 Sterilizer, Steris Corporation, Mentor, Ohio. The devices were exposed horizontally in the sterilizer for 2, 4, 6, 8, 10 and 12 minutes. The vacuum and pressure pulse for each cycle used a vacuum level of 25.4 cm of mercury (10 inches Hg) and a pressure pulse of 0.2 MPa (16 psig).

The numbers of indicators detecting a sterilization failure are shown in Table 6. Three STERIGAGE and three ATTEST BIs were tested in each device configuration listed in the table.

TABLE 6

| | No. | 2 min | | | 4 min | | | 6 min | | |
| --- | --- | --- | --- | --- | --- | --- | --- | --- | --- | --- |
| SB | Tested | SG | 3 h | G | SG | 3 h | G | SG | 3 h | G |
| Full | 3 | 3 | 3 | 3 | 3 | 3 | 3 | 3 | 3 | 3 |
| R-80 | 3 | 3 | 3 | 3 | 3 | 3 | 3 | 2 | 1 | 1 |
| R-60 | 3 | 3 | 3 | 3 | 1 | 1 | 0 | 0 | 1 | 1 |
| R-50 | 3 | 3 | 3 | 3 | 1 | 1 | 0 | 0 | 0 | 0 |
| Full-L | 2 | 3 | 3 | 3 | 3 | 3 | 3 | 3 | 3 | 3 |
| R-80-L | 2 | 3 | 3 | 3 | 3 | 3 | 3 | 3 | 3 | 3 |
| R-60-L | 2 | 3 | 3 | 3 | 3 | 3 | 3 | 3 | 3 | 3 |
| R-50-L | 2 | 3 | 3 | 3 | 3 | 3 | 3 | 1 | 1 | 1 |

| | No. | 8 min | | | 10 min | | |
| --- | --- | --- | --- | --- | --- | --- | --- |
| SB | Tested | SG | 3 h | G | SG | 3 h | G |
| Full | 3 | 3 | 3 | 3 | 2 | 1 | 1 |
| R-80 | 3 | 0 | 0 | 0 | 0 | 0 | 0 |
| R-60 | 3 | 0 | 0 | 0 | 0 | 0 | 0 |
| R-50 | 3 | 0 | 0 | 0 | 0 | 0 | 0 |
| Full-L | 2 | 3 | 3 | 2 | 2 | 1 | 1 |
| R-80-L | 2 | 2 | 2 | 2 | 1 | 0 | 0 |

TABLE 6-continued

| | | | | | | | |
|---|---|---|---|---|---|---|---|
| R-60-L | 2 | 0 | 1 | 1 | 0 | 0 | 0 |
| R-50-L | 2 | 0 | 0 | 0 | 0 | 0 | 0 |

SB = solid body.
3 h = after 3 hours incubation.
G = growth.
SG = STERIGAGE

The results with the polypropylene inserts were similar to the results obtained in Example 3 using the DELRIN® acetal resin inserts.

Example 6

Increased the Size of the Aluminum Container from 138 cm³ (4.6 ounce) to 187 cm³ (6.3 ounce)

Example 3 was repeated except that the aluminum containers were increased in size from 138 cm³ to 187 cm³.

The numbers of indicators detecting a sterilization failure are shown in Table 7. The number of devices tested in each configuration is listed in the table under "No. Tested".

TABLE 7

| | No. | 2 min | | | 4 min | | | 6 min | | |
|---|---|---|---|---|---|---|---|---|---|---|
| SB | Tested | SG | 3 h | G | SG | 3 h | G | SG | 3 h | G |
| Full | 3 | 3 | 3 | 3 | 3 | 3 | 3 | 3 | 3 | 3 |
| R-80 | 3 | 3 | 3 | 3 | 3 | 3 | 3 | 3 | 3 | 3 |
| R-60 | 3 | 3 | 3 | 3 | 3 | 3 | 2 | 2 | 1 | 1 |
| R-50 | 3 | 3 | 3 | 3 | 2 | 1 | 0 | 1 | 1 | 1 |
| Full-L | 2 | 2 | 2 | 2 | 2 | 2 | 2 | 2 | 2 | 2 |
| R-80-L | 2 | 2 | 2 | 2 | 2 | 2 | 2 | 2 | 2 | 2 |
| R-60-L | 2 | 2 | 2 | 2 | 2 | 2 | 2 | 2 | 2 | 2 |
| R-50-L | 2 | 2 | 2 | 2 | 2 | 2 | 2 | 2 | 2 | 2 |
| 1-Layer Paper | 3 | 3 | 3 | 3 | 3 | 3 | 3 | 3 | 3 | 2 |
| | 3 | 3 | 3 | 3 | 0 | 1 | 0 | 0 | 0 | 0 |

| | No. | 8 min | | | 10 min | | | 12 min | | |
|---|---|---|---|---|---|---|---|---|---|---|
| SB | Tested | SG | 3 h | G | SG | 3 h | G | SG | 3 h | G |
| Full | 3 | 3 | 3 | 3 | 3 | 3 | 3 | 3 | 3 | 2 |
| R-80 | 3 | 3 | 2 | 1 | 2 | 1 | 1 | 0 | 0 | 0 |
| R-60 | 3 | 0 | 1 | 0 | 0 | 0 | 0 | 0 | 0 | 0 |
| R-50 | 3 | 0 | 0 | 0 | 0 | 0 | 0 | 0 | 0 | 0 |
| Full-L | 2 | 2 | 2 | 2 | 2 | 2 | 2 | 2 | 2 | 2 |
| R-80-L | 2 | 2 | 2 | 2 | 1 | 1 | 1 | 0 | 0 | 0 |
| R-60-L | 2 | 1 | 1 | 1 | 0 | 1 | 1 | 0 | 0 | 0 |
| R-50-L | 2 | 1 | 1 | 1 | 0 | 0 | 0 | 0 | 0 | 0 |
| 1-Layer Paper | 3 | 0 | 2 | 1 | 0 | 0 | 0 | 0 | 0 | 0 |
| | 3 | 0 | 0 | 0 | 0 | 0 | 0 | 0 | 0 | 0 |

| | No. | 14 min | | | 16 min | | |
|---|---|---|---|---|---|---|---|
| SB | Tested | SG | 3 h | G | SG | 3 h | G |
| Full | 3 | 0 | 0 | 0 | 1 | 0 | 0 |
| R-80 | 3 | 0 | 0 | 0 | 0 | 0 | 0 |
| R-60 | 3 | 0 | 0 | 0 | 0 | 0 | 0 |
| R-50 | 3 | 0 | 0 | 0 | 0 | 0 | 0 |
| Full-L | 2 | 2 | 1 | 1 | 0 | 0 | 0 |
| R-80-L | 2 | 0 | 0 | 0 | 0 | 0 | 0 |
| R-60-L | 2 | 0 | 0 | 0 | 0 | 0 | 0 |
| R-50-L | 2 | 0 | 0 | 0 | 0 | 0 | 0 |
| 1-Layer Paper | 3 | 0 | 0 | 0 | 0 | 0 | 0 |

TABLE 7-continued

| Layer Paper | 3 | 0 | 0 | 0 | 0 | 0 | 0 |
|---|---|---|---|---|---|---|---|

SB = solid body.
3 h = after 3 hours incubation.
G = growth.
SG = STERIGAGE

Increasing the can size from 138 cm³ to 187 cm³ significantly increased the resistance to the steam sterilization process. For example, in Example 2, using the 138 cm³ (4.6 ounce) cans and the full insert, the ATTEST BIs were killed after the 10 minute exposure time. In this example, the full insert in the larger 187 cm³ (6.3 ounce) can required 14 minutes to inactivate the ATTEST BIs.

Example 7

Increased the Size of the Aluminum can from 138 cm³ (4.6 Ounce) and 187 cm³ (6.3 Ounce) to 262 cm³ (8.8 Ounce)

This example is the same as Example 6, except the can size was increased from 187 cm³ (6.3 ounce) to 262 cm³ (8.8 ounce). The aluminum can is illustrated in FIG. 1.

The devices were exposed in a 132° C. (270° F.) 4 pulse pre-vacuum sterilizer, AMSCO® Eagle Model 3013 Sterilizer, Steris Corporation, Mentor, Ohio. The cans were exposed horizontally for 6, 8, 10, 12, 14 and 16 minutes. The vacuum and pressure pulse for each cycle used a vacuum level of 25.4 cm of mercury (10 inches Hg) and a pressure pulse of 0.2 MPa (16 psig).

The numbers of indicators detecting a sterilization failure are shown in Table 8. The number of devices tested in each configuration is listed in the table under "No. Tested".

TABLE 8

| | No. | 6 min | | | 8 min | | | 10 min | | |
|---|---|---|---|---|---|---|---|---|---|---|
| SB | Tested | SG | 3 h | G | SG | 3 h | G | SG | 3 h | G |
| Full | 3 | 3 | 3 | 3 | 3 | 3 | 3 | 3 | 3 | 3 |
| R-80 | 3 | 3 | 3 | 3 | 3 | 2 | 2 | 2 | 2 | 0 |
| R-60 | 3 | 3 | 3 | 3 | 3 | 1 | 0 | 0 | 0 | 0 |
| R-50 | 3 | 3 | 3 | 3 | 2 | 1 | 1 | 0 | 0 | 0 |
| Full-L | 2 | 2 | 2 | 2 | 2 | 2 | 2 | 2 | 2 | 2 |
| R-80-L | 2 | 2 | 2 | 2 | 2 | 2 | 2 | 2 | 2 | 1 |
| R-60-L | 2 | 2 | 2 | 2 | 2 | 2 | 2 | 2 | 2 | 0 |
| R-50-L | 2 | 2 | 2 | 2 | 2 | 2 | 2 | 0 | 0 | 0 |
| 1-Layer Paper | 3 | 3 | 3 | 3 | 1 | 2 | 1 | 0 | 0 | 0 |
| | 3 | 0 | 0 | 0 | 0 | 0 | 0 | 0 | 0 | 0 |

| | No. | 12 min | | | 14 min | | | 16 min | | |
|---|---|---|---|---|---|---|---|---|---|---|
| SB | Tested | SG | 3 h | G | SG | 3 h | G | SG | 3 h | G |
| Full | 3 | 3 | 3 | 1 | 3 | 2 | 1 | 1 | 0 | 0 |
| R-80 | 3 | 1 | 0 | 0 | 0 | 0 | 0 | 0 | 0 | 0 |
| R-60 | 3 | 0 | 0 | 0 | 0 | 0 | 0 | 0 | 0 | 0 |
| R-50 | 3 | 0 | 0 | 0 | 0 | 0 | 0 | 0 | 0 | 0 |
| Full-L | 2 | 2 | 2 | 2 | 2 | 2 | 2 | 2 | 2 | 1 |
| R-80-L | 2 | 1 | 1 | 0 | 0 | 1 | 0 | 0 | 0 | 0 |
| R-60-L | 2 | 0 | 0 | 0 | 0 | 0 | 0 | 0 | 0 | 0 |
| R-50-L | 2 | 0 | 0 | 0 | 0 | 0 | 0 | 0 | 0 | 0 |
| 1- | 3 | 0 | 0 | 0 | 0 | 0 | 0 | 0 | 0 | 0 |

TABLE 8-continued

| Layer | | | | | | | | | | |
|---|---|---|---|---|---|---|---|---|---|---|
| Paper | 3 | 0 | 0 | 0 | 0 | 0 | 0 | 0 | 0 | 0 |

SB = solid body.
3 h = after 3 hours incubation.
G = growth.
SG = STERIGAGE

Increasing the can size from 187 cm³ (6.3 ounce) to 262 cm³ (8.8 ounce), increased the resistance to the steam sterilization process. For example, in Example 6, using the 187 cm³ (6.3 ounce) cans with the full insert, the ATTEST BIs were killed after the 14 minute exposure time. In this example, the full insert in the larger 262 cm³ (8.8 ounce) can required 16 minutes to inactivate the ATTEST BIs.

Table 9 compares the indicator results in the 138 cm³ (4.6 ounce) and 187 cm³ (6.3 ounce) to 262 cm³ (8.8 ounce) cans when tested with the Full and Full-L inserts.

TABLE 9

| Can | | No. | 2 min | | | 4 min | | |
|---|---|---|---|---|---|---|---|---|
| Size | SB | Tested | SG | 3 h | G | SG | 3 h | G |
| 138 cm³ | Full | 3 | 3 | 3 | 3 | 3 | 3 | 3 |
| 187 cm³ | Full | 3 | 3 | 3 | 3 | 3 | 3 | 3 |
| 262 cm³ | Full | 3 | NT | NT | NT | NT | NT | NT |
| 138 cm³ | Full-L | 2 | 2 | 2 | 2 | 2 | 2 | 2 |
| 187 cm³ | Full-L | 2 | 2 | 2 | 2 | 2 | 2 | 2 |
| 262 cm³ | Full-L | 2 | NT | NT | NT | NT | NT | NT |

| Can | | No. | 6 min | | | 8 min | | |
|---|---|---|---|---|---|---|---|---|
| Size | SB | Tested | SG | 3 h | G | SG | 3 h | G |
| 138 cm³ | Full | 3 | 3 | 3 | 2 | 2 | 1 | 1 |
| 187 cm³ | Full | 3 | 3 | 3 | 3 | 3 | 3 | 3 |
| 262 cm³ | Full | 3 | 3 | 3 | 3 | 3 | 3 | 3 |
| 138 cm³ | Full-L | 2 | 2 | 2 | 2 | 2 | 2 | 2 |
| 187 cm³ | Full-L | 2 | 2 | 2 | 2 | 2 | 2 | 2 |
| 262 cm³ | Full-L | 2 | 2 | 2 | 2 | 2 | 2 | 2 |

| Can | | No. | 10 min | | | 12 min | | |
|---|---|---|---|---|---|---|---|---|
| Size | SB | Tested | SG | 3 h | G | SG | 3 h | G |
| 138 cm³ | Full | 3 | 1 | 0 | 0 | NT | NT | NT |
| 187 cm³ | Full | 3 | 3 | 3 | 3 | 3 | 3 | 2 |
| 262 cm³ | Full | 3 | 3 | 3 | 3 | 3 | 3 | 1 |
| 138 cm³ | Full-L | 2 | 2 | 1 | 0 | NT | NT | NT |
| 187 cm³ | Full-L | 2 | 2 | 2 | 2 | 2 | 2 | 2 |
| 262 cm³ | Full-L | 2 | 2 | 2 | 2 | 2 | 2 | 2 |

| Can | | No. | 14 min | | | 16 min | | |
|---|---|---|---|---|---|---|---|---|
| Size | SB | Tested | SG | 3 h | G | SG | 3 h | G |
| 138 cm³ | Full | 3 | NT | NT | NT | NT | NT | NT |
| 187 cm³ | Full | 3 | 0 | 0 | 0 | 1 | 0 | 0 |
| 262 cm³ | Full | 3 | 3 | 2 | 1 | 1 | 0 | 0 |
| 138 cm³ | Full-L | 2 | NT | NT | NT | NT | NT | NT |
| 187 cm³ | Full-L | 2 | 2 | 1 | 1 | 0 | 0 | 0 |
| 262 cm³ | Full-L | 2 | 2 | 2 | 2 | 2 | 2 | 1 |

SB = solid body.
3 h = after 3 hours incubation.
G = growth.
SG = STERIGAGE
NT = not tested The data demonstrates the influence of the can size on the resistance of the indicators exposed to the sterilization process.

Example 8

Sterilant Access 0.2 cm Hole in Cap and 1-Liner

Example 2 was repeated except the sterilant access was provided using a 0.2 cm (0.081 inch) diameter hole in the cap and one paper liner under the cap as illustrated in FIG. 3.

The devices were exposed in a 132° C. (270° F.) 4 pulse pre-vacuum sterilizer, AMSCO® Eagle Model 3013 Sterilizer, Steris Corporation, Mentor, Ohio. The cans were exposed in the vertical position for 2, 4, 6, 8, 10 and 12 minutes. The vacuum and pressure pulse for each cycle used a vacuum level of 25.4 cm of mercury (10 inches Hg) and a pressure pulse of 0.2 MPa (16 psig).

The numbers of indicators detecting a sterilization failure are shown in Table 10. Three devices were tested for each configuration listed in the table.

TABLE 10

| | No. | 2 min | | | 4 min | | | 6 min | | |
|---|---|---|---|---|---|---|---|---|---|---|
| SB | Tested | SG | 3 h | G | SG | 3 h | G | SG | 3 h | G |
| Full | 3 | 3 | 3 | 3 | 3 | 3 | 3 | 3 | 3 | 3 |
| R-80 | 3 | 3 | 3 | 3 | 3 | 3 | 3 | 3 | 3 | 3 |
| R-60 | 3 | 3 | 3 | 3 | 3 | 3 | 3 | 3 | 3 | 3 |
| R-50 | 3 | 3 | 3 | 3 | 3 | 3 | 3 | 2 | 3 | 3 |
| Full-L | 2 | 3 | 3 | 3 | 3 | 3 | 3 | 3 | 3 | 3 |
| R-80-L | 2 | 3 | 3 | 3 | 3 | 3 | 3 | 3 | 3 | 3 |
| R-60-L | 2 | 3 | 3 | 3 | 3 | 3 | 3 | 2 | 3 | 3 |
| R-50-L | 2 | 3 | 3 | 3 | 3 | 3 | 3 | 3 | 3 | 3 |
| 1-Layer Paper | 3 | 3 | 3 | 3 | 3 | 3 | 3 | 3 | 3 | 3 |
| | 3 | 0 | 3 | 3 | 0 | 0 | 0 | 0 | 1 | 0 |

| | No. | 8 min | | | 10 min | | | 12 min | | |
|---|---|---|---|---|---|---|---|---|---|---|
| SB | Tested | SG | 3 h | G | SG | 3 h | G | SG | 3 h | G |
| Full | 3 | 3 | 3 | 3 | 3 | 3 | 3 | 3 | 3 | 3 |
| R-80 | 3 | 3 | 3 | 3 | 3 | 2 | 2 | 0 | 2 | 1 |
| R-60 | 3 | 3 | 3 | 2 | 0 | 1 | 1 | 0 | 1 | 0 |
| R-50 | 3 | 0 | 3 | 3 | 0 | 1 | 0 | 0 | 0 | 0 |
| Full-L | 2 | 3 | 3 | 3 | 3 | 3 | 3 | 3 | 3 | 3 |
| R-80-L | 2 | 3 | 3 | 3 | 3 | 3 | 3 | 3 | 2 | 2 |
| R-60-L | 2 | 3 | 3 | 3 | 1 | 3 | 3 | 1 | 3 | 1 |
| R-50-L | 2 | 2 | 3 | 3 | 0 | 3 | 1 | 0 | 0 | 0 |
| 1-Layer Paper | 3 | 2 | 3 | 3 | 0 | 3 | 3 | 0 | 1 | 0 |
| | 3 | 0 | 0 | 0 | 0 | 0 | 0 | 0 | 0 | 0 |

SB = solid body.
3 h = after 3 hours incubation.
G = growth.
SG = STERIGAGE

The results were similar to the results in Example 2 demonstrating that the sterilant access can be provided by several methods.

Example 9

Sterilant Access

Two 0.41 cm Holes in Cap and 1-Liner

Example 8 was repeated except the two 0.41 cm (0.161 inch) diameter holes were drilled into the cap and one paper liner was used in the cap as illustrated in FIG. 3. The devices were exposed horizontally in this example.

The devices were exposed in a 132° C. (270° F.) 4 pulse pre-vacuum sterilizer, AMSCO® Eagle Model 3013 Sterilizer, Steris Corporation, Mentor, Ohio. The cans were exposed in the horizontal position for 2, 4, 6, 8 and 10 minutes. The vacuum and pressure pulse for each cycle used a vacuum level of 25.4 cm of mercury (10 inches Hg) and a pressure pulse of 0.2 MPa (16 psig).

The numbers of indicators detecting a sterilization failure are shown in Table 11. Three devices were tested for each configuration listed in the table.

TABLE 11

| SB | No. Tested | 2 min SG | 2 min 3 h | 2 min G | 4 min SG | 4 min 3 h | 4 min G | 6 min SG | 6 min 3 h | 6 min G |
|---|---|---|---|---|---|---|---|---|---|---|
| Full | 3 | 3 | 3 | 3 | 3 | 3 | 3 | 3 | 3 | 3 |
| R-80 | 3 | 3 | 3 | 3 | 3 | 3 | 3 | 3 | 2 | 2 |
| R-60 | 3 | 3 | 3 | 3 | 1 | 3 | 1 | 1 | 0 | 0 |
| R-50 | 3 | 3 | 3 | 3 | 3 | 2 | 0 | 0 | 0 | 0 |
| Full-L | 2 | 3 | 3 | 3 | 3 | 3 | 3 | 3 | 3 | 3 |
| R-80-L | 2 | 3 | 3 | 3 | 3 | 3 | 3 | 3 | 3 | 3 |
| R-60-L | 2 | 3 | 3 | 3 | 3 | 3 | 3 | 3 | 1 | 1 |
| R-50-L | 2 | 3 | 3 | 3 | 3 | 3 | 3 | 2 | 1 | 0 |
| 1-Layer Paper | 3 | 3 | 3 | 3 | 3 | 3 | 3 | 3 | 2 | 1 |
| | 3 | 3 | 0 | 0 | 0 | 0 | 0 | 0 | 0 | 0 |

| SB | No. Tested | 8 min SG | 8 min 3 h | 8 min G | 10 min SG | 10 min 3 h | 10 min G |
|---|---|---|---|---|---|---|---|
| Full | 3 | 3 | 2 | 2 | 3 | 2 | 2 |
| R-80 | 3 | 3 | 1 | 0 | 3 | 0 | 0 |
| R-60 | 3 | 0 | 0 | 0 | 0 | 0 | 0 |
| R-50 | 3 | 0 | 0 | 0 | 0 | 0 | 0 |
| Full-L | 2 | 3 | 3 | 3 | 3 | 3 | 3 |
| R-80-L | 2 | 3 | 3 | 3 | 3 | 1 | 0 |
| R-60-L | 2 | 3 | 0 | 0 | 0 | 0 | 0 |
| R-50-L | 2 | 0 | 0 | 0 | 0 | 0 | 0 |
| 1-Layer Paper | 3 | 0 | 0 | 0 | 0 | 0 | 0 |
| | 3 | 0 | 0 | 0 | 0 | 0 | 0 |

SB = solid body.
3 h = after 3 hours incubation.
G = growth.
SG = STERIGAGE

This example further demonstrates an alternate method of providing sterilant access for the can.

Example 10

Adjustable Tortuous Path Device

A prototype was made of stainless steel as illustrated in FIG. 4. The prototype consists of a top (cap) and bottom component which are connected by a threaded connection, like a jar and lid. When the cap is connected to the bottom component, a tortuous pathway is created between the threads in the two components. This pathway presents a challenge for air removal and steam penetration into the housing where the biological and chemical indicators are located. The path length can be adjusted by increasing the number of turns the cap is turned onto the bottom component. Increasing the path length increases the time to inactivate the indicators. Additional resistance to the sterilization process can be further increased by adding a DELRIN® acetal resin insert to the inside of the prototype. The prototype can be constructed of different materials such as DELRIN® acetal resin, TEFLON® brand material, other thermoplastics, aluminum and stainless steel.

The ATTEST™ 1292 Rapid Biological Indicators (ATTEST BIs) available from 3M Company, St. Paul, Minn., were placed in the tortuous path device or placed inside machined DELRIN® acetal resin inserts. The Full XL described in FIG. 1A and the Reduced insert described in FIG. 1F were evaluated. DELRIN® acetal resin is available from E.I. du Pont de Nemours and Company, Wilmington, Del.

The devices were exposed in a 132° C. (270° F.) 4 pulse pre-vacuum sterilizer, AMSCO® Eagle Model 3013 Sterilizer, Steris Corporation, Mentor, Ohio. The device was exposed in a vertical position with the cap upright for the exposure times listed in Table 12. The vacuum and pressure pulse for each cycle used a vacuum level of 25.4 cm of mercury (10 inches Hg) and a pressure pulse of 0.28 MPa (26 psig).

The ATTEST BI fluorescence and growth results are shown in Table 12 for the different configurations tested.

TABLE 12

| Table | Exposure (min) | No. Turns | SB | 1292 3 h | 1292 G | 1292 Cap Orientation |
|---|---|---|---|---|---|---|
| 12.A | 1 | 5 | None | Pos | Pos | Cap Up |
| | 2 | 5 | None | Pos | Pos | Cap Up |
| | 3 | 5 | None | Neg | Neg | Cap Up |
| | 4 | 5 | None | Neg | Neg | Cap Up |
| | 4 | 5 | None | Neg | Neg | Cap Up |
| | 4 | 5 | None | Neg | Neg | Cap Up |
| 12.B | 3 | 10 | None | Pos | Pos | Cap Up |
| | 4 | 10 | None | Pos | Neg | Cap Up |
| | 4 | 10 | None | Pos | Neg | Cap Up |
| | 4 | 10 | None | Pos | Neg | Cap Up |
| | 5 | 10 | None | Neg | Neg | Cap Up |
| | 6 | 10 | None | Neg | Neg | Cap Up |
| | 6 | 10 | None | Neg | Neg | Cap Up |
| | 10 | 10 | None | Neg | Neg | Cap Up |
| | 10 | 10 | None | Neg | Neg | Cap Up |
| 12.C | 4 | 5 | Full | Pos | Pos | Cap Up |
| | 8 | 5 | Full | Pos | Pos | Cap Up |
| | 12 | 5 | Full | Neg | Pos | Cap Up |
| | 16 | 5 | Full | Neg | Neg | Cap Up |
| 12.D | 4 | 5 | Full | Pos | Pos | Cap Down |
| | 8 | 5 | Full | Pos | Pos | Cap Down |
| | 12 | 5 | Full | Pos | Neg | Cap Down |
| | 16 | 5 | Full | Neg | Neg | Cap Down |
| 12.E | 8 | 10 | Full | Pos | Pos | Cap Down |
| | 10 | 10 | Full | Pos | Pos | Cap Down |
| | 12 | 10 | Full | Pos | Pos | Cap Down |
| | 15 | 10 | Full | Pos | Pos | Cap Down |
| | 20 | 10 | Full | Neg | Neg | Cap Down |
| 12.F | 1 | 5 | Reduced | Pos | Pos | Down |
| | 2 | 5 | Reduced | Pos | Pos | Down |
| | 4 | 5 | Reduced | Pos | Pos | Down |
| | 3 | 5 | Reduced | Pos | Pos | Down |
| | 6 | 5 | Reduced | Pos | Pos | Down |
| | 8 | 5 | Reduced | Pos | Neg | Down |
| | 10 | 5 | Reduced | Neg | Neg | Down |

SB = solid body.
3 h = after 3 hours incubation.
G = growth.

With 5 cap turns (12.A), the ATTEST BIs were inactivated after 3 minutes. Increasing the number of turns to 10 (12.B), increased the kill time to 5 minutes. With 5 turns and the Full insert (12.0 and 12.D), the ATTEST BIs were not inactivated until 16 minutes. The orientation of the BI inside the insert (12.C and 12.D) did not have any effect on the kill time. Using the Full insert and increasing the number of turns to 10 (12.E), increased the kill time to 20 minutes. Reducing the insulating properties of the insert (12.F), decreased the kill time 10 minutes.

Example 11

Material Comparison

The Full inserts (FIG. 1A) made of different materials were compared using the 138 cm³ (4.6 ounce) cans. The cans were vented using the 3 cap liners and assembled as in FIG. 1 except using three rather than one liner. The inserts were made of DELRIN® acetal resin, polypropylene, aluminum, stainless steel (316), oak, and polyester.

The devices were exposed in a 132° C. (270° F.) 4 pulse pre-vacuum sterilizer, AMSCO® Eagle Model 3013 Sterilizer, Steris Corporation, Mentor, Ohio. The cans were exposed in the horizontal position for 2, 4, 6, 8, 10 and 12 minutes. The vacuum and pressure pulse for each cycle used a vacuum level of 25.4 cm of mercury (10 inches Hg) and a pressure pulse of 0.2 MPa (16 psig).

The numbers of indicators detecting a sterilization failure are shown in Table 13. Three devices were tested for each configuration listed in the table.

TABLE 13

| Full SB | Ave. Weight (g) | No. Tested | 2 min SG | 3 h | G | 4 min SG | 3 h | G | 6 min SG | 3 h | G |
|---|---|---|---|---|---|---|---|---|---|---|---|
| DELRIN | 100 | 3 | 3 | 3 | 3 | 3 | 3 | 3 | 3 | 3 | 3 |
| PP | 63 | 3 | 3 | 3 | 3 | 3 | 3 | 3 | 3 | 3 | 3 |
| Alum. | 189 | 3 | 3 | 0 | 0 | 0 | 0 | 0 | 0 | 0 | 0 |
| SS | 553 | 3 | 3 | 3 | 3 | 1 | 1 | 1 | 0 | 1 | 0 |
| Polyester | 50 | 3 | 3 | 3 | 3 | 1 | 3 | 2 | 2 | 1 | 1 |
| Oak | 87 | 3 | 3 | 3 | 3 | 2 | 0 | 0 | 0 | 0 | 0 |

| Full SB | Ave. Weight (g) | No. Tested | 8 min SG | 3 h | G | 10 min SG | 3 h | G | 12 min SG | 3 h | G |
|---|---|---|---|---|---|---|---|---|---|---|---|
| DELRIN | 100 | 3 | 3 | 3 | 3 | 3 | 3 | 1 | 3 | 3 | 1 |
| PP | 63 | 3 | 3 | 2 | 2 | 2 | 1 | 0 | 2 | 2 | 1 |
| Alum. | 189 | 3 | 0 | 0 | 0 | 0 | 0 | 0 | 0 | 0 | 0 |
| SS | 553 | 3 | 0 | 0 | 0 | 0 | 0 | 0 | 0 | 0 | 0 |
| Polyester | 50 | 3 | 1 | 1 | 0 | 0 | 0 | 0 | 0 | 0 | 0 |
| Oak | 87 | 3 | 0 | 0 | 0 | 0 | 0 | 0 | 0 | 0 | 0 |

SB = solid body.
3 h = after 3 hours incubation.
G = growth.
SG = STERIGAGE
PP = polypropylene
Alum. = aluminum
SS = stainless steel (316)

The ATTEST BIs in the DELRIN® acetal resin and polypropylene inserts were not inactivated after 12 minutes of exposure. In the aluminum inserts, the BIs were killed after 2 minutes. The stainless steel inserts were inactivated after 8 minutes and the BIs in the polyester insert required 10 minutes of exposure to inactivate the BI. BIs in the oak inserts were inactivated after 4 minutes.

Example 12

Large Inserts

Larger diameter DELRIN® acetal resin inserts were evaluated in the 452 cm³ (15.3 ounces) aluminum cans. The inserts are shown in FIGS. 1A, 1C, 1D, 1E, 1F, and 1G.

The nested design shown in FIG. 1E has three cylinders or layers machined out of DELRIN® acetal resin. Each cylinder has a different inside and outside diameter. The inside and outside diameters are sized to allow the smallest cylinder to fit inside the second largest cylinder and the second largest cylinder can fit into the largest cylinder. The sterilization challenge can easily be modified by adding or removing the cylinders or layers.

The Notched Bottom (Top portion of solid body of FIG. 1G) and Notched Center (FIG. 1G) are similar to the Full XL insert (FIG. 1A) except for the indicator orientation and location.

The devices were exposed in a 132° C. (270° F.) 4 pulse pre-vacuum sterilizer, AMSCO® Eagle Model 3013 Sterilizer, Steris Corporation, Mentor, Ohio. The cans were exposed in the horizontal position for 10, 12, 14, 16, 18 and 20 minutes. The vacuum and pressure pulse for each cycle used a vacuum level of 25.4 cm of mercury (10 inches Hg) and a pressure pulse of 0.2 MPa (16 psig).

The numbers of indicators detecting a sterilization failure are shown in Table 14.

TABLE 14

| SB | No. Tested | 10 min SG | 3 h | G | 12 min SG | 3 h | G | 14 min SG | 3 h | G |
|---|---|---|---|---|---|---|---|---|---|---|
| Full | 3 | 3 | 3 | 3 | 3 | 3 | 3 | 3 | 3 | 3 |
| R-60 | 3 | 3 | 3 | 2 | 3 | 2 | 1 | 1* | 0 | 0 |
| R-50 | 3 | 2* | 1 | 1 | 1 | 1 | 0 | 0 | 0 | 0 |
| 3-layer | 3 | 3 | 3 | 3 | 2 | 3 | 2 | 1 | 3 | 2 |
| 2-layer | 3 | 2 | 3 | 3 | 2 | 3 | 3 | 1 | 3 | 1 |
| 1-layer | 3 | 1 | 3 | 0 | 0 | 0 | 0 | 0 | 0 | 0 |
| Notched Bottom | 2 | 2 | 2 | 1 | 2 | 1 | 1 | 1 | 0 | 0 |
| Notched Center | 2 | 2 | 2 | 2 | 1 | 2 | 1 | 2 | 2 | 1 |

| SB | No. Tested | 16 min SG | 3 h | G | 18 min SG | 3 h | G | 20 min SG | 3 h | G |
|---|---|---|---|---|---|---|---|---|---|---|
| Full | 3 | 3 | 3 | 3 | 3 | 3 | 2 | 3 | 3 | 0 |
| R-60 | 3 | 0 | 0 | 0 | 0 | 0 | 0 | 0 | 0 | 0 |
| R-50 | 3 | 0 | 0 | 0 | 0 | 0 | 0 | 0 | 0 | 0 |
| 3-layer | 3 | 2 | 3 | 2 | 3 | 3 | 1 | 1 | 3 | 1 |
| 2-layer | 3 | 2 | 3 | 0 | 0 | 2 | 0 | 0 | 2 | 0 |
| 1-layer | 3 | 0 | 0 | 0 | 0 | 0 | 0 | 0 | 0 | 0 |
| Notched Bottom | 2 | 1 | 0 | 0 | 0 | 0 | 0 | 0 | 0 | 0 |
| Notched Center | 2 | 2 | 1 | 0 | 1 | 1 | 0 | 0 | 0 | 0 |

*crushed can
SB = solid body.
3 h = after 3 hours incubation.
G = growth.
SG = STERIGAGE The data shows with the Full, R-60 and R-50 inserts the time to inactive the indicators can be reduced by reducing the material surrounding the indicators. The same effect is demonstrated with the Nested inserts by removing the number of cylinders or layers surrounding the indicators. The Notched insert demonstrates the effect of the indicators orientation and location within the container. The indicators exposed with the Notched inserts were inactivated faster than inside the Full insert.

Example 13

Compare a Small Diameter to Large Diameter Insert

In this example, two inserts with the same wall thickness but different internal diameters were tested to demonstrate the effect of having the insulating body in close proximity to the sterilization indicators. The 1-layer insert (FIG. 1A) with an internal diameter of 1.27 cm (0.5 inches) was compared to 1-layer insert with an internal diameter of 2.8 cm (1.09 inches) (FIG. 1A).

The ATTEST™ 1292 Rapid Biological Indicators (ATTEST BIs) and COMPLY™ STERIGAGE™ 1243 Steam Chemical Integrator (STERIGAGE), both available from 3M Company, St. Paul, Minn., were placed inside machined DELRIN® acetal resin inserts described in FIG. 1A.

The STERIGAGE and ATTEST BIs were rolled up together inside an absorbent paper towel approximately 14 by 13 cm (5.5 by 5.1 inches). The paper towel is commercially available as Kleenex® Premiere®, Kimberly-Clark, Roswell, Ga. FIG. 1 illustrates the assembly. The inserts were placed inside 262 cm$^3$ (8.8 ounce) aluminum screw cap cans shown in FIG. 1 and commercially available from Elemental Container, Inc. Union, N.J. Three paper liners were placed under the cap, as shown in FIG. 1, to provide a tortuous path sterilant access between the cap and the can body threads. The paper liners were made of a blotter paper with an average caliper of 0.0508-0.0559 cm (20-22 mils), an average porosity of 10 to 20 sec/100 cm$^3$ and a basis weight (43.18 cm×55.88 cm (17 inches×22 inches)/500 sheets) of 40-44.5 kg (88-98 lbs). The paper is commercially available from Monadnock Paper Mills, Inc. Bennington, N.H. The complete assembly is illustrated in FIG. 1 except that three instead of one liner were used.

The devices were exposed in a 132° C. (270° F.) 4 pulse pre-vacuum sterilizer, AMSCO® Eagle Model 3013 Sterilizer, Steris Corporation, Mentor, Ohio. The cans were exposed horizontally in the sterilizer for 4, 6, 8 and 10 minutes. The vacuum and pressure pulse for each cycle used a vacuum level of 25.4 cm of mercury (10 inches Hg) and a pressure pulse of 0.2 MPa (16 psig).

The numbers of indicators detecting a sterilization failure are shown in Table 15. Three STERIGAGE and three ATTEST BIs were tested in each device configuration listed in the table.

TABLE 15

| SB | No. Tested | 4 min SG | 4 min 3 h | 4 min G | 6 min SG | 6 min 3 h | 6 min G | 8 min SG | 8 min 3 h | 8 min G | 10 min SG | 10 min 3 h | 10 min G |
|---|---|---|---|---|---|---|---|---|---|---|---|---|---|
| Small Dia. | 3 | 3 | 3 | 3 | 3 | 3 | 3 | 1 | 3 | 3 | 0 | 2 | 0 |
| Large Dia. | 3 | 0 | 3 | 3 | 0 | 2 | 0 | 0 | 0 | 0 | 0 | 0 | 0 |

SB = solid body.
3 h = after 3 hours incubation.
G = growth.
SG = STERIGAGE

The insert with the large internal diameter for holding the sterilization indicators did not provide the same thermal protection as the smaller diameter insert which was in close proximity to the indicators. The ATTEST BIs were killed after 8 minutes in the large diameter insert compared to all surviving the 8 minute exposure in the small diameter insert.

Weights of the Inserts:
The inserts referred to in the above Examples had weights shown in Table 16 below.

TABLE 16

| Material | SB | Ave. Wt grams |
|---|---|---|
| Delrin | Full | 99.4 |
|  | R-80 | 77.4 |
|  | R-60 | 65.0 |
|  | R-50 | 53.5 |
|  | Full-L | 131.9 |
|  | R-80-L | 102.8 |
|  | R-60-L | 86.2 |
|  | R-50-L | 70.8 |
|  | Full XL | 199.6 |
|  | R-60 XL | 132.3 |
|  | R-50 XL | 109.4 |
|  | Reduced | 137.1 |
|  | 1 layer | 40.6 |
|  | Nested 1 layer + base | 65.1 |
|  | Nested 2 layer + base | 136.2 |
|  | Nested 3 layer + base | 237.9 |
|  | Notched | 194.7 |
| Polypropylene | Full | 63.3 |
|  | R-80 | 49.5 |
|  | R-60 | 41.3 |
|  | R-50 | 34.0 |
|  | Full-L | 84.0 |
|  | R-80-L | 65.8 |
|  | R-60-L | 55.0 |
|  | R-50-L | 45.2 |

Example 14

An ATTEST™ Rapid 5 Test Pack Plus (available from 3M Company, St. Paul, Minn.) was placed into a machined DELRIN® acetal resin case as shown in FIG. 8, except that the case included three manifolds 896, each with one manifold entrance into space 825 rather than the three manifold entrances into space 825 in manifold 896 shown in FIG. 8. DELRIN® acetal resin is available from E.I. du Pont de Nemours and Company, Wilmington, Del. The DELRIN® acetal resin case was tightened using six bolts (not shown in FIG. 8) to hold top (830B) and bottom (830A) tightly together. Once the top and bottom were secured together, the tortuous path could be modified using six set screws, one in each opening 895 associated with each of the three manifolds 896, which block entrances into the test pack chamber. The set screws could be completely sealed by covering the openings 895 with TEFLON® brand tape. Manipulating these set screws and tape allowed the case to be used in either a 10 min or 20 min 132° C. (270° F.) 4 pulse pre-vacuum sterilization cycle.

The case with the ATTEST™ Rapid 5 Test Pack Plus was exposed in a 132° C. (270° F.) 4 pulse pre-vacuum sterilizer, AMSCO® Eagle Model 3013 Sterilizer, Steris Corporation, Mentor, Ohio. The case was exposed for 4, 5, and 10 minutes. The vacuum and pressure pulse for each cycle used a vacuum level of 25.4 cm of mercury (10 inches Hg) and a pressure pulse of 0.2 MPa (16 psig). The case was also evaluated in a sterilizer fault condition by introducing a greater than 25 mm Hg/min air leak into the chamber during the vacuum phase of the cycle. Air leaks are a common failure mode for pre-vacuum steam sterilizers.

After exposure, the STERIGAGE™ chemical integrators from the Test Packs were read to determine if the moving front indicator dye had moved into the Reject or Accept region of the indicator. The ATTEST BIs were activated by crushing the inner ampules and incubating the indicators in the ATTEST™ Model 290 Autoreaders (3M Company, St. Paul, Minn.) which detects the fluorescence caused by the enzymatic breakdown of an enzyme substrate in the growth medium. After 3 hours of incubation, the Autoreader activates a green light indicating an acceptable sterilization cycle or a red light is activated to indicate a fluorescent positive indicator and a sterilization cycle failure. The indicators continued incubating for a total of 48 hours at 60° C. to allow surviving spores to grow and cause a visual color change in the growth medium from purple to yellow. The color change to yellow indicates a sterilization failure.

The results are shown in Table 17. The data shows that the case is capable of being modified by changing the restricted flow of gas and sterilant into the test pack. In Cycles 6-10, with none or up to 4 of the 6 set screws removed, the sterilization indicators indicated a sterilization failure in 4 of 5 cycles with a 4 or 5 minute exposure time. In Cycle 11, all of the set screws were removed, and the indicators indicated an acceptable sterilization process in the 5 minute sterilization time. The indicators in Cycles 1-3 indicated a sterilization failure in a 10 minute sterilization time when all the set screws were covered with tape to further reduce flow into the case. In Cycles 4 and 5, tape was not used to cover the set screws and the sterilization indicators indicated an acceptable sterilization cycle. The indicators inside the case indicated a sterilization failure in the air leak fault condition in Cycle 12.

TABLE 17

| Cycle No. | Time (min) | Set Screws Covered with tape | Set Screws Removed | SG | Biological Indicator 3 h | Biological Indicator G |
|---|---|---|---|---|---|---|
| 1 | 10 | 6 | None | Reject | + | + |
| 2 | 10 | 4 End Hole | None | Reject | + | + |
| 3 | 10 | 2 Center Holes | None | Reject | + | + |
| 4 | 10 | None | 2 Center Holes | Accept | − | − |
| 5 | 10 | None | None | Accept | − | − |
| 6 | 5 | None | None | Accept | − | − |
| 7 | 4 | None | None | Reject | + | + |
| 8 | 5 | None | None | Reject | + | + |
| 9 | 5 | None | 2 Center Holes | Reject | + | + |
| 10 | 5 | None | 4 End Holes | Accept | + | + |
| 11 | 5 | None | 6 All Holes | Accept | − | − |
| 12 | 5-with air leak | None | 6 All Holes | Reject | + | + |

3 h = after 3 hours incubation.
G = growth.
SG = STERIGAGE

All references and publications or portions thereof cited herein are expressly incorporated herein by reference in their entirety into this disclosure. Exemplary embodiments of this invention are discussed and reference has been made to some possible variations within the scope of this invention. These and other variations and modifications in the invention will be apparent to those skilled in the art without departing from the scope of the invention, and it should be understood that this invention is not limited to the exemplary embodiments set forth herein. Accordingly, the invention is to be limited only by the claims provided below and equivalents thereof.

What is claimed is:

1. A sterilization process challenge device comprising:
   a solid body comprised of walls which define a space, wherein the space fully contains a sterilization indicator and a volume of gas of at least 5 cubic centimeters and not more than 1000 cubic centimeters;
   a flow restrictor associated with the solid body such that any flow of the gas out of the space and any flow of a sterilant into the space is restricted;
   wherein the sterilization indicator indicates whether or not it has been contacted by the sterilant for a time and at a temperature sufficient to sterilize an article;
   wherein the walls of the solid body are impervious to the sterilant, and wherein the walls have a thickness of at least 0.5 centimeter.

2. The device of claim 1, further comprising a container, wherein the solid body is sealed within the container, the flow restrictor is attached to or is part of the container, and any gas flow out of and any sterilant flow into the container are restricted by the flow restrictor.

3. The device of claim 2, wherein a volume of gas of at least 5 cubic centimeters is contained within the container in addition to the volume of gas contained in the space defined by the walls of the solid body.

4. The device of claim 3, wherein the container comprises at least one wall which is flexible.

5. The device of claim 4, wherein the volume of gas varies by at least 10 percent as a pressure differential varies between inside and outside the container.

6. The device of claim 1, wherein a layer of material, which absorbs a condensate of the sterilant, separates the sterilization indicator and the walls of the solid body.

7. The device of claim 1, wherein the flow restrictor comprises at least one pressure-actuating valve, which is actuated when there is a pressure difference across the valve.

8. The device of claim 7, wherein the at least one pressure-actuating valve is at least two pressure-actuating valves; and wherein the at least two pressure-actuating valves are each independently actuated when there is pressure differences across the respective valves.

9. A kit comprising at least one sterilization process challenge device of claim 1; and a plurality of sterilization indicators for the same or different sterilization processes.

* * * * *